United States Patent [19]

Leppard et al.

[11] Patent Number: 5,411,847
[45] Date of Patent: May 2, 1995

[54] COLOR-PHOTOGRAPHIC RECORDING MATERIAL

[75] Inventors: David G. Leppard, Marly; Hugh S. Laver, Reinach, both of Switzerland

[73] Assignee: Ciba-Geigy Corporation, Ardsley, N.Y.

[21] Appl. No.: 114,130

[22] Filed: Aug. 30, 1993

[30] Foreign Application Priority Data

Sep. 1, 1992 [CH] Switzerland .................. 2731/92

[51] Int. Cl.$^6$ .................. G03C 1/34; G03C 7/392
[52] U.S. Cl. .................. 430/551; 430/554; 430/555; 430/558
[58] Field of Search .............. 430/551, 554, 555, 558

[56] References Cited

U.S. PATENT DOCUMENTS

| | | | |
|---|---|---|---|
| 4,549,015 | 10/1985 | Howell | 549/87 |
| 4,588,679 | 5/1989 | Furutachi | 430/551 |
| 4,616,082 | 10/1986 | Howell | 544/87 |
| 4,631,252 | 12/1986 | Howell | 430/551 |
| 4,971,995 | 11/1990 | Schoofs et al. | 514/520 |
| 5,049,482 | 9/1991 | Nishijima et al. | 430/551 |
| 5,068,172 | 11/1991 | Seto et al. | 430/551 |

FOREIGN PATENT DOCUMENTS

| | | |
|---|---|---|
| 0327455 | 2/1989 | European Pat. Off. |
| 0357442 | 9/1989 | European Pat. Off. |
| 0384393 | 8/1990 | European Pat. Off. |
| 54-73032 | 6/1979 | Japan .................. 430/551 |
| 62-42153 | 2/1987 | Japan. |

OTHER PUBLICATIONS

Derwent Abst. 87-091059.

*Primary Examiner*—Lee C. Wright
*Attorney, Agent, or Firm*—Luther A. R. Hall

[57] ABSTRACT

A color-photographic recording material is described which contains a magenta coupler and, as stabilizer, at least one compound of the formula

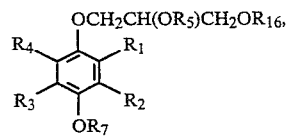

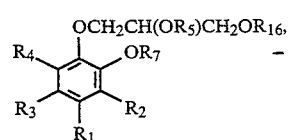

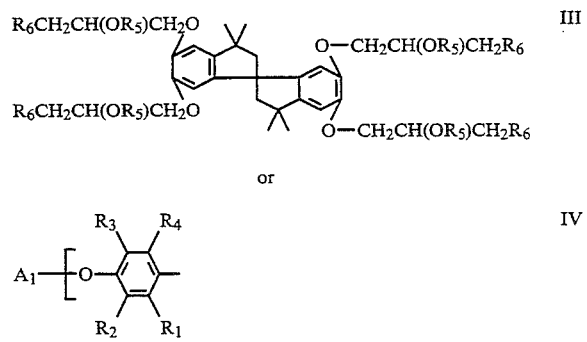

$$-OCH_2CH(OR_5)CH_2OR_{19}OCH_2CH(OR_5)CH_2\underset{m}{\overline{\rule{0pt}{1em}}}A_2$$

where the radicals are as defined in claim 1.

8 Claims, No Drawings

COLOR-PHOTOGRAPHIC RECORDING MATERIAL

The present invention relates to a novel colour-photographic recording material which contains a magenta coupler and, as light stabilizer, a hydroxyalkyl hydroquinone ether.

The alkylated hydroquinone ethers or diethers used hitherto as stabilizers in photographic materials exhibited inadequate activity, in particular in the case of 1H-pyrazolo-[5,1-c][1,2,4]triazole magenta couplers (see also structure C-5). The photostability of the magenta dyes was inadequate. In addition, the colour couplers had hitherto to be predissolved in high-boiling oils before they could be dispersed in the gelatin. Although some known stabilizers would in principle have been suitable as coupler oils, they have side effects, for example sensitometric effects, wavelength shifts of the dye absorption, or yellowing on weathering or in an Atlas tester, and were therefore unsatisfactory.

A group of hydroxyalkyl hydroquinone ethers has now been found which, surprisingly, has proved substantially free from such disadvantages. In addition, they are also suitable as coupler oils and thus facilitate a simplified incorporation of the couplers. In particular, this group of hydroquinones is suitable for increasing the stability of magenta dyes in colour-photographic materials.

The novel stabilizers can be used for all types of photosensitive materials. For example, they can be employed for colour paper, colour reversal paper, direct-positive colour material, colour negative film, colour positive film, colour reversal film, etc. They are preferably used, inter alia, for photosensitive colour material which contains a reversal substrate or forms positives.

Colour-photographic recording materials usually contain, on a support, a blue-sensitive and/or a green-sensitive and/or a red-sensitive silver-halide emulsion layer and, if desired, a protection layer, the stabilizer for the magenta dye being in the green-sensitive layer.

The present application thus relates to a colour-photographic recording material which contains a magenta coupler and, as stabilizer, at least one compound of the formula

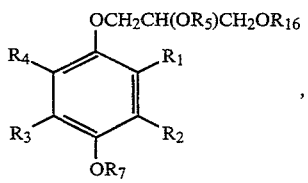   I

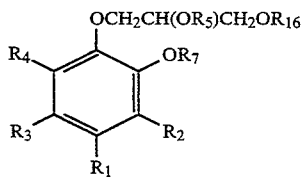   II

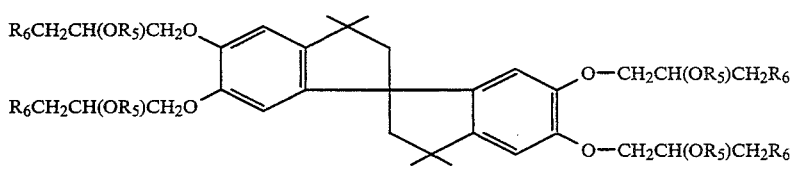   III or

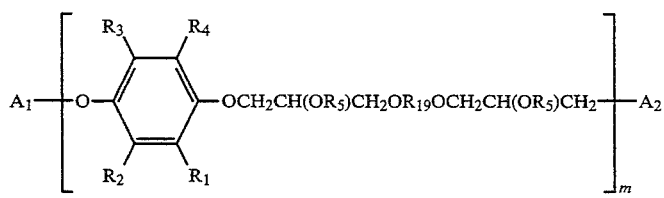   IV where

R$_1$ and R$_3$, independently of one another, are hydrogen, C$_1$-C$_{12}$alkyl, C$_5$-C$_7$cycloalkyl, which is unsubstituted or substituted by one or two C$_1$-C$_4$alkyl groups, or are phenyl-C$_1$-C$_4$alkyl, phenyl, C$_1$-C$_8$alkoxy or a group of the formula V

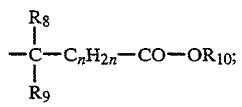   V in which R$_8$ and R$_9$, independently of one another, are C$_1$-C$_8$alkyl;

n is 1-10, and R$_{10}$ is hydrogen, C$_1$-C$_{24}$alkyl, which is unsubstituted or interrupted by one or more —O— atoms and is unsubstituted or substituted by one —OH group, or is C$_2$-C$_{18}$alkenyl, C$_5$-C$_{12}$cycloalkyl, which is unsubstituted or substituted by 1 to 3 C$_1$-C$_4$alkyl, or is phenyl, which is unsubstituted or substituted by one or two C$_1$-C$_4$alkyl, or is phenyl-C$_1$-C$_4$alkyl or furfuryl;

$R_2$ and $R_4$, independently of one another, are hydrogen or $C_1$-$C_{12}$alkyl;

$R_5$ is hydrogen, —CO—$R_{11}$, —CO—$OR_{12}$ or —Si($R_{13}$)($R_{14}$)($R_{15}$), in which $R_{11}$ is $C_1$-$C_{18}$alkyl, $C_2$-$C_{18}$alkenyl or phenyl; $R_{12}$ is $C_1$-$C_4$alkyl and $R_{13}$, $R_{14}$ and $R_{15}$, independently of one another, are $C_1$-$C_6$alkyl or phenyl; the radicals $R_6$, independently of one another, are —$OR_{16}$ or $C_1$-$C_{15}$alkyl, in which $R_{16}$ is hydrogen, $C_1$-$C_{18}$alkyl, $C_2$-$C_{18}$alkenyl, phenyl-$C_1$-$C_4$alkyl, $C_3$$C_{24}$alkyl or $C_2$-$C_{14}$hydroxyalkyl, each of which is interrupted by one or more O atoms, or is phenyl, which is unsubstituted or substituted by $C_1$-$C_4$alkyl, $C_1$-$C_4$alkoxy or halogen, tolyl, $C_5$-$C_6$cycloalkyl, which is unsubstituted or substituted by 1 to 3 $C_1$-$C_8$alkyl, or is —CO—$R_{11}$, in which $R_{11}$ is $C_1$-$C_{18}$alkyl, $C_2$-$C_{18}$alkenyl or phenyl;

$R_7$ is hydrogen, $C_1$-$C_{12}$alkyl, which is uninterrupted or interrupted by one or more —O—, —S— or —$SO_2$— groups, $C_5$-$C_{12}$cycloalkyl, which is unsubstituted or substituted by 1 to 3 $C_1$-$C_4$alkyl, or is phenyl-$C_1$-$C_4$alkyl, a group of the formula VI $$-\underset{\underset{R_{17}}{|}}{CH}-CO-OR_{18}, \qquad VI$$

or a group of the formula VII $$-CH_2CH(OR_5)CH_2R_6 \qquad VII,$$

in which $R_5$ and $R_6$ are as defined for formula I, $R_{17}$ is hydrogen or $C_1$-$C_{18}$alkyl, and $R_{18}$ is $C_1$-$C_{12}$alkyl, which is unsubstituted or interrupted by one or more —O— atoms, or is $C_2$-$C_{18}$alkenyl, benzyl or phenyl, which is unsubstituted or substituted by 1-3 $C_1$-$C_4$alkyl;

$R_{19}$ is $C_2$-$C_{10}$alkylene, phenylene or a-phenylene-$R_{20}$-phenylene- group, in which $R_{20}$ is —O—, —S—, —$SO_2$—, —$CH_2$— or —C($CH_3$)$_2$;

m is 1-100;

$A_1$ is hydrogen, —$CH_2CH(OR_5)CH_2OR_{19}OCH(OR_5)CH_2OR_5$ or $$-CH_2CH(OR_5)CH_2OR_{19}OCH_2CH\overset{O}{\overset{|}{-\!\!\!-\!\!\!-}}CH_2;$$

and
$A_2$ is —OH or

[structure: benzene ring with $R_3$, $R_4$, $R_2$, $R_1$ substituents, —O— and —$OA_1$;]

or $R_3$ and $R_7$ in the formula I, together with the atoms to which they are bonded, form a $C_5$-$C_6$ ring, which is unsubstituted or substituted by 1 to 3 $C_1$-$C_8$alkyl.

Any $C_1$-$C_{24}$alkyl substitutents in the compounds according to the invention are radicals such as methyl, ethyl, propyl, butyl, pentyl, hexyl, heptyl, octyl, nonyl, decyl, undecyl, dodecyl, tetradecyl, hexadecyl and octadecyl, and corresponding branched isomers.

$C_5$-$C_{12}$cycloalkyl radicals are, for example, cyclopentyl, cyclohexyl, cyclooctyl or cyclododecyl.

Alkyl radicals having 3 to 24 carbon atoms which are interrupted by oxygen are, for example, —($CH_2$C$H_2$O)$_{1-11}CH_3$ and —($CH_2CH_2$O)$_{1-11}CH_2CH_3$.

Alkenyl radicals having 2 to 18 carbon atoms may be monounsaturated or, from 4 carbon atoms, polyunsaturated.

Alkylene radicals having 2 to 10 carbon atoms can be derived from corresponding alkyl radicals.

$C_1$-$C_8$alkoxy radicals are, for example, methoxy, ethoxy, propoxy, butoxy or hexoxy and corresponding branched isomers.

Preference is given to stabilizers of the formula

[structure I: benzene ring with $R_4$, $R_1$, $R_3$, $R_2$, $OR_7$, and $OCH_2CH(OR_5)CH_2OR_{16}$ substituents]

[structure II: benzene ring with $R_4$, $OR_7$, $R_3$, $R_2$, $R_1$, and $OCH_2CH(OR_5)CH_2OR_{16}$ substituents]

[structure III: fluorene-type spiro structure with $R_6CH_2CH(OR_5)CH_2O$ and O—$CH_2CH(OR_5)CH_2R_6$ groups]

or

[structure IV: $A_1\!\!-\!\!\!\left[\!\!-O-\text{benzene ring }(R_3, R_4, R_2, R_1)\!\!-\!\!\right]$ ]

$$-OCH_2CH(OR_5)CH_2OR_{19}OCH_2CH(OR_5)CH_2\!\!-\!\!\!\!\underset{m}{\rceil}\!\!-\!\!A_2$$

in which $R_1$ and $R_3$, independently of one another, are hydrogen, $C_1$-$C_8$alkyl, cyclohexyl, —C($CH_3$)$_2C_6H_5$, $C_1$-$C_4$alkoxy or a group of the formula V $$-\underset{\underset{R_9}{|}}{\overset{\overset{R_8}{|}}{C}}-C_nH_{2n}-CO-OR_{10}, \qquad V$$

in which $R_8$ and $R_9$ are methyl;

n is 3, and $R_{10}$ is hydrogen, $C_1$-$C_{12}$alkyl, which is unsubstituted or interrupted by one or more —O— atoms and is unsubstituted or substituted by one —OH, or is $C_2$-$C_{18}$alkenyl or benzyl;

$R_2$ is hydrogen;

$R_4$ is hydrogen or $C_1$-$C_8$alkyl;

$R_5$ is hydrogen, —CO—$R_{11}$, —CO—$OR_{12}$ or —Si($R_{13}$)($R_{14}$)($R_{15}$), in which $R_{11}$ is $C_1$-$C_{18}$alkyl, $C_2$-$C_{18}$alkenyl or phenyl, $R_{12}$ is $C_1$-$C_4$alkyl, and $R_{13}$, $R_{14}$ and $R_{15}$, independently of one another, are $C_1$-$C_6$alkyl or phenyl; the radicals $R_6$ independently of one another, are —$OR_{16}$, in which $R_{16}$ is hydrogen, $C_1$-$C_{18}$alkyl, $C_2$-$C_{18}$alkenyl, phenyl-$C_1$-$C_4$alkyl, $C_3$-$C_{24}$alkyl or $C_2$-$C_{14}$hydroxyalkyl, each of which is interrupted by one or more O atoms, or is phenyl, tolyl, $C_5$-$C_6$cycloalkyl, which is unsubstituted or substituted by 1 to 3 $C_1$-$C_8$alkyl, or is —CO—$R_{11}$, in which $R_{11}$ is $C_1$-$C_{18}$alkyl, $C_2$-$C_{18}$alkenyl or phenyl; $R_7$ is $C_1$-$C_4$alkyl, a group of the formula VI

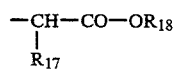
VI or a group of the formula VII

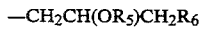
VII, in which $R_5$ and $R_6$ are as defined for formula I,
$R_{17}$ is hydrogen or $C_1$-$C_{12}$alkyl, and $R_{18}$ is $C_1$-$C_8$alkyl;
$R_{19}$ is $C_2$-$C_8$alkylene, phenylene or a -phenylene-$R_{20}$-phenylene- group, in which $R_{20}$ is —$SO_2$—, —$CH_2$— or —$C(CH_3)_2$—;
m is 1–50;
$A_1$ is hydrogen, —$CH_2CH(OR_5)CH_2OR_{19}OCH(OR_5)CH_2OR_5$ or

—$CH_2CH(OR_5)CH_2OR_{19}OCH_2CH$⟨$O$⟩$CH_2$;

and

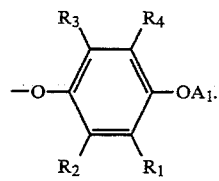

Particular preference is given to stabilizers of the formulae

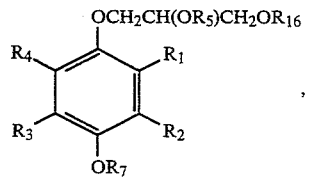
I

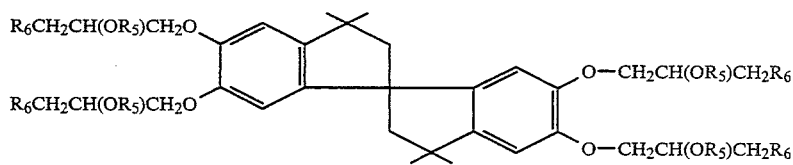
III or

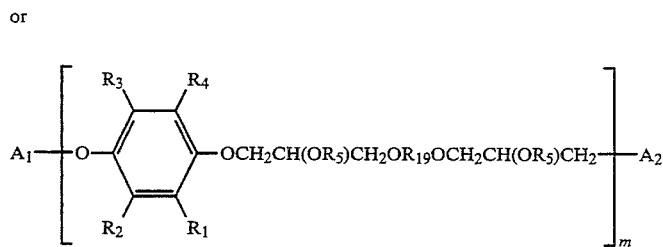
IV in which $R_1$ and $R_3$, independently of one another, are hydrogen, $C_1$-$C_8$alkyl, $C_1$-$C_4$alkoxy or a group of the formula V $$-\underset{R_9}{\overset{R_8}{\underset{|}{\overset{|}{C}}}}-C_nH_{2n}-CO-OR_{10},$$
V in which $R_8$ and $R_9$ are methyl,
n is 3, and
$R_{10}$ is $C_1$-$C_4$alkyl;
$R_2$ is hydrogen;
$R_4$ is hydrogen or $C_1$-$C_8$alkyl;
$R_5$ is hydrogen, —CO—$R_{11}$, —COO$R_{12}$ or —Si($R_{13}$)($R_{14}$)($R_{15}$), in which $R_{11}$ is $C_1$-$C_4$alkyl or $C_2$-$C_3$alkenyl, $R_{12}$ is $C_1$-$C_4$alkyl, and $R_{13}$, $R_{14}$ and $R_{15}$, independently of one another, are $C_1$-$C_6$alkyl;
the radicals $R_6$, independently of one another, are —$OR_{16}$, in which $R_{16}$ is $C_1$-$C_{18}$alkyl, allyl, benzyl, phenyl, $C_3$-$C_{12}$alkyl which is interrupted by one or more O atoms, or is cyclohexyl or —CO—$R_{11}$, in which $R_{11}$ is $C_1$-$C_4$alkyl or $C_2$-$C_3$alkenyl;
$R_7$ is a group of the formula VII

VII, in which $R_5$ and $R_6$ are as defined for formula I;
$R_{19}$ is $C_2$-$C_8$alkylene or a phenylene-$R_{20}$-phenylene- group, in which $R_{20}$ is —$C(CH_3)_2$—;
m is 1–25;
$A_1$ is hydrogen, —$CH_2CH(OR_5)CH_2OR_{19}OCH(OR_5)CH_2OR_5$ or

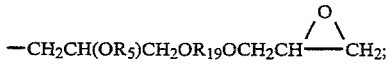

and
$A_2$ is —OH or

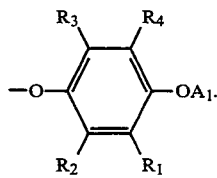

Of particular significance are stabilizers of the formula

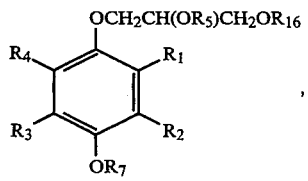

in which
R$_1$, R$_3$ and R$_4$, independently of one another, are hydrogen or C$_1$-C$_8$alkyl;
R$_2$ is hydrogen;
R$_5$ is hydrogen or —CO—CH$_3$;
R$_{16}$ is C$_1$-C$_{12}$alkyl, allyl or C$_3$-C$_7$alkyl which is interrupted by 1–3 O atoms; and
R$_7$ is a group of the formula VII

—CH$_2$CH(OR$_5$)CH$_2$R$_6$      VII, in which R$_5$ is as defined for formula I and R$_6$ is —OR$_{16}$.

Very particular preference is given to stabilizers of the formula

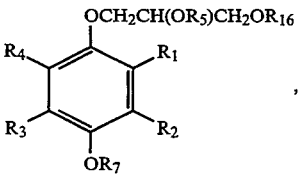

in which
R$_1$, R$_3$ and R$_4$, independently of one another, are hydrogen or C$_1$-C$_8$ alkyl;
R$_2$ is hydrogen;
R$_5$ is hydrogen;
R$_{16}$ is C$_1$-C$_{12}$alkyl, and
R$_7$ is a group of the formula VII

—CH$_2$CH(OR$_5$)CH$_2$R$_6$      VII, in which R$_5$ is as defined for formula 1 and R$_6$ is —OR$_{16}$.

The novel material preferably contains gelatin interlayers between the silver-halide emulsion layers.

Preference is given to photographic materials of this type in which the silver-halide in the blue-sensitive and/or green-sensitive and/or red-sensitive layer is silver chloride bromide comprising at least 90 mol % of silver chloride.

Preference is furthermore given to photographic materials which contain the silver-halide emulsion layers in the sequence blue-sensitive, green-sensitive and red-sensitive layers.

Typical and preferred stabilizers according to the invention are the following:

Examples

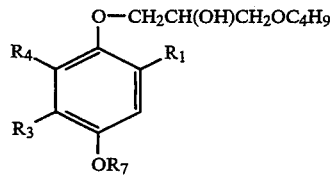

| No. | R$_1$ | R$_3$ | R$_4$ | R$_7$ |
|---|---|---|---|---|
| 1. | C(CH$_3$)$_3$ | C(CH$_3$)$_3$ | H | CH$_2$CH(OH)CH$_2$OC$_4$H$_9$ |
| 2. | C(CH$_3$)$_3$ | C(CH$_3$)$_3$ | H | H |
| 3. | OC$_4$H$_9$ | OC$_4$H$_9$ | H | CH$_2$CH(OH)CH$_2$OC$_4$H$_9$ |
| 4. | OC$_4$H$_9$ | OC$_4$H$_9$ | H | H |
| 5. | C(CH$_3$)$_2$(CH$_2$)$_3$CO—OCH$_3$ | C(CH$_3$)$_2$(CH$_2$)$_3$CO—OCH$_3$ | H | CH$_2$CH(OH)CH$_2$OC$_4$H$_9$ |
| 6. | C(CH$_3$)$_2$(CH$_2$)$_3$CO—OCH$_3$ | C(CH$_3$)$_2$(CH$_2$)$_3$CO—OCH$_3$ | H | H |
| 7. | C(CH$_3$)$_2$CH$_2$C(CH$_3$)$_3$ | H | H | CH$_2$CH(OH)CH$_2$OC$_4$H$_9$ |
| 8. | H | C(CH$_3$)$_2$CH$_2$C(CH$_3$)$_3$ | H | H |
| 9. | C(CH$_3$)$_2$CH$_2$C(CH$_3$)$_3$ | C(CH$_3$)$_2$CH$_2$C(CH$_3$)$_3$ | H | CH$_2$CH(OH)CH$_2$OC$_4$H$_9$ |
| 10. | C(CH$_3$)$_2$CH$_2$C(CH$_3$)$_3$ | C(CH$_3$)$_2$CH$_2$C(CH$_3$)$_3$ | H | H |
| 11. | C(CH$_3$)$_3$ | H | H | CH$_2$(CH$_{12}$H$_{25}$)CO—OC$_2$H$_5$ |
| 12. | H | H | H | CH$_2$CH(OH)CH$_2$OC$_4$H$_9$ |
| 13. | CH$_3$ | CH$_3$ | CH$_3$ | CH$_2$CH(OH)CH$_2$OC$_4$H$_9$ |
| 14. | CH$_3$ | CH$_3$ | H | CH$_2$CH(OH)CH$_2$OC$_4$H$_9$ |
| 15. | H | C(CH$_3$)$_3$ | H | H |
| 16. | CH$_3$ | H | H | CH$_2$CH(OH)CH$_2$OC$_4$H$_9$ |
| 17. | H | H | H | C$_{12}$H$_{25}$ |
| 18. | CH$_3$ | CH$_3$ | H | C$_{12}$H$_{25}$ |
| 19. | H | CH$_3$ | CH$_3$ | CH$_2$CH(OH)CH$_2$OC$_4$H$_9$ |
| 20. | C(CH$_3$)$_3$ | H | H | CH$_2$CH(OH)CH$_2$OC$_4$H$_9$ |

-continued

Examples

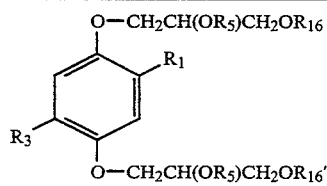

| No. | $R_1$ | $R_3$ | $R_5$ | $R_{16} = R_{16}'$ |
|---|---|---|---|---|
| 21 | $C(CH_3)_3$ | $C(CH_3)_3$ | H | $CH_2CH_2OCH_3$ |
| 22 | $C(CH_3)_3$ | $C(CH_3)_3$ | $CO-CH_3$ | $CH_2CH_2O-CO-CH_3$ |
| 23 | $C(CH_3)_3$ | $C(CH_3)_3$ | $CO-CH_3$ | $CH_2CH_2OCH_3$ |
| 24 | $C(CH_3)_3$ | $C(CH_3)_3$ | $CO-CH_3$ | $C_4H_9$ |
| 25 | $C(CH_3)_3$ | $C(CH_3)_3$ | $CO-C_4H_9$ | $C_4H_9$ |
| 26 | $C(CH_3)_3$ | $C(CH_3)_3$ | $CO-CH_3$ | $CO-CH_3$ |
| 27 | $C(CH_3)_3$ | $C(CH_3)_3$ | $Si(CH_3)_2[C(CH_3)_2CH(CH_3)_2]$ | $C_4H_9$ |
| 28 | $C(CH_3)_3$ | H | H | H |
| 29 | $CH_3$ | H | H | H |
| 30 | $CH_3$ | $CH_3$ | H | H |
| 31 | $C(CH_3)_3$ | $C(CH_3)_3$ | H | $CH_2CH(OH)CH_2OCH_2CH(C_2H_5)-C_4H_9$ |
| 32 | $C(CH_3)_3$ | $C(CH_3)_3$ | H | $CH_2CH_2OH$ |

| No. | $R_1$ | $R_3$ | $R_5$ | $R_{16}/R_{16}'$ |
|---|---|---|---|---|
| 32/a | $CH_3$ | H | H | $CH_2CH(C_2H_5)C_4H_9$ |
| 32/b | $CH_3$ | $CH_3$ | H | $CH_2CH(C_2H_5)C_4H_9$ |
| 32/c | $CH_3$ | H | H | $C_6H_5$ |
| 32/d | $CH_3$ | H | H | $CH(CH_3)_2$ |
| 32/e | $CH_3$ | H | H | $CH_2CH=CH_2$ |
| 32/f | $CH_3$ | H | H | $CH_2CH(CH_3)_2$ |
| 32/g | $CH_3$ | $CH_3$ | H | $CH(CH_3)_2$ |
| 32/h | $CH_3$ | H | H | $CH_2C_6H_5$ |
| 32/i | $CH_3$ | H | H | $C(CH_3)_3$ |
| 32/j | $CH_3$ | H | H | Cyclohexyl |
| 32/k | $C(CH_3)_3$ | $C(CH_3)_3$ | H | $C_6H_5$ |
| 32/l | $CH_3$ | $CH_3$ | $COCH_3$ | $C_4H_9$ |
| 32/m | $CH_3$ | H | $CH_3$ | $C_4H_9$ |
| 32/n | $CH_3$ | $CH_3$ | $CH_3$ | $C_4H_9$ |
| 33 | $CH_3$ | $CH_3$ | H | $C_4H_9/CH_2(C_2H_5)C_4H_9$ |
| 34 | $CH_3$ | $CH_3$ | H | $C(CH_3)_3/C_4H_9$ |
| 35 | $C(CH_3)_3$ | $C(CH_3)_3$ | H | $CH_2CH(C_2H_5)C_4H_9/C(CH_3)_3$ |
| 36 | $C(CH_3)_3$ | $C(CH_3)_3$ | H | $CH_2CH(CH_3)_2/C(CH_3)_3$ |
| 37 | $CH_3$ | $CH_3$ | H | $CH_2CH(CH_3)_2/C(CH_3)_3$ |
| 38 | $CH_3$ | CH | H | $CH_2CH(CH_3)_2/C_4H_9$ |
| 39 | $CH_3$ | H | H | $CH_2CH(CH_3)_2/C_4H_9$ |
| 40 | $CH_3$ | H | H | $CH_2CH(CH_3)_2/CH_2CH_2CH(CH_3)_2$ |
| 41 | $C(CH_3)_3$ | H | H | $CH_2CH(CH_3)_2/C_6H_5$ |
| 41/a | $C(CH_3)_2C_2H_5$ | $C(CH_3)_2C_2H_5$ | H | $C(CH_3)_3/C_4H_9$ |
| 41/b | $CH_3$ | $CH_3$ | H | $(CH_2CH_2O)CH_3/(CH_2CH_2O)_2C_2H_5$ |
| 41/c | $CH_3$ | $CH_3$ | H | $C(CH_3)_3/C_4H_9$ |
| 41/d | $CH_3$ | $CH_3$ | H | $C_5H_{11}/CH_2CH_2CH(CH_3)_2$ |
| 41/e | $CH_3$ | H | H | $C(CH_3)_3/C_4H_9$ |
| 41/f | $CH_3$ | $CH_3$ | H | $C_{12}H_{25}/C_{13}H_{27}/C_{14}H_{29}$ |
| 41/g | $C(CH_3)_3$ | H | H | $C_6H_4-OCH_3$ (para) |
| 41/h | $C(CH_3)_3$ | $C(CH_3)_3$ | H | $C_6H_4-OCH_3$ (para) |
| 41/i | $CH_3$ | H | H | $C_6H_4-OCH_3$ (para) |
| 41/j | H | H | H | $C_6H_4-OCH_3$ (para) |
| 41/k | $C(CH_3)_3$ | $C(CH_3)_3$ | H | $C_6H_5$ |
| 41/l | $C(CH_3)_3$ | H | H | $C_6H_5$ |
| 41/m | $C(CH_3)_3$ | H | H | $C_6H_5$ |

| | -continued |
|---|---|
| | Examples |
| 42 | 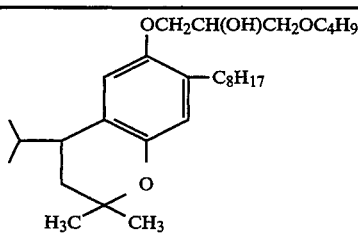 |
| 43 | 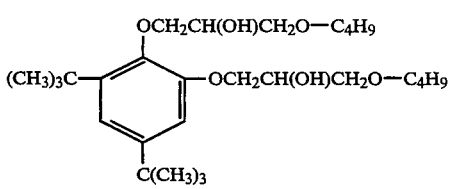 |

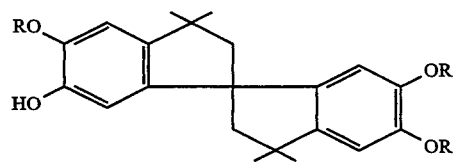

| No. | R |
|---|---|
| 44 | —CH$_2$CH(OH)CH$_2$OC$_4$H$_9$ |
| 45 | —CH$_2$CH(OH)CH$_2$OCH$_2$CH(C$_2$—H$_5$)C$_4$H$_9$ |
| 46 | —CH$_2$CH(OH)CH$_2$OC$_{13}$H$_{27}$(C$_{15}$H$_{31}$) |
| 47 | 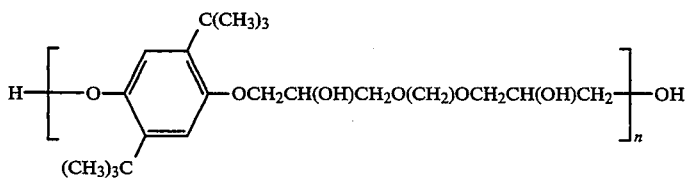 |
| | 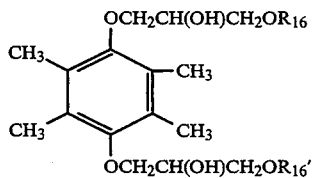 |
| 48 | R$_{16}$ = R$_{16}'$ = C$_4$H$_9$ |
| 49 | R$_{16}$ = R$_{16}'$ = CH$_2$CH(C$_2$H$_5$)C$_4$H$_9$ |
| 50 | 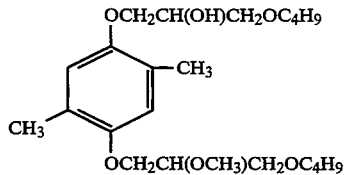 |

Usually the stabilizers according to the present invention are employed in a 0.1 to 4-fold, preferably 0.2 to 2-fold, amount by weight, based on the conjointly used color coupler.

The magenta couplers in the colour-photographic recording material can be, for example, simple 1-aryl-5-pyrazolones or pyrazole derivatives which are fused to 5-membered heterocyclic rings, e.g. imidazopyrazoles, pyrazolopyrazoles, pyrazolotriazoles or pyrazolotetrazoles.

A group of magenta couplers comprises 5-pyrazolones of the formula C

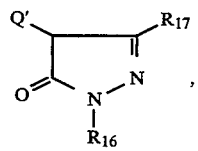 (C)

as described in British Patent 2 003 473. In this formula, R$_{16}$ is hydrogen, alkyl, aryl, alkenyl or a heterocyclic group. R$_{17}$ is hydrogen, alkyl, aryl, a heterocyclic group, an ester group, an alkoxy group, an akkylthio group, a carboxyl group, an arylamino group, an acylamino group, a (thio)urea group, a (thio)carbamoyl group, a guanidino group or a sulfonamido group.

$R_{17}$ is preferably a

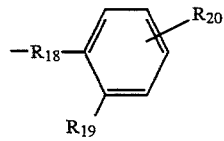

group, in which $R_{18}$ is imino, acylamino or ureido, $R_{19}$ is hydrogen, halogen, alkyl or alkoxy, $R_{20}$ is hydrogen, alkyl, acylamino, carbamoyl, sulfamoyl, sulfonamido, alkoxycarbonyl, acyloxy or a urethane group.

If Q' is hydrogen, the magenta coupler is tetraequivalent with respect to the silver-halide.

Preferred examples of magenta couplers of this type are compounds of the formula

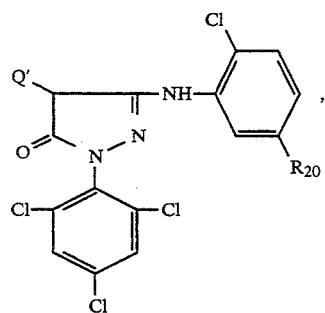

(C-1)

in which $R_{20}$ is as defined above, and Q', as described above, is a leaving group. These compounds are preferably present in the material according to the invention.

Further examples of tetraequivalent magenta couplers of this type are given in U.S. Pat. Nos. 2,983,608, 3,061,432, 3,062,653, 3,127,269, 3,152 896, 3,311,476, 3,419,391, 3,519429, 3,558,319, 3,582,322, 3,615,506, 3,684,514, 3,834,908, 3,888,680, 3,891,445, 3,907,571, 3,928,044, 3,930,861, 3,930,866 and 3,933,500 and JP-A89/309 058.

If Q' in the formula C is not hydrogen, but instead a group which is eliminated during the reaction with the oxidized developer, the magenta coupler is diequivalent. In this case, Q can be, for example, halogen or a group bonded to the pyrazole ring via O, S or N. Diequivalent couplers of this type give greater colour density and are more reactive towards the oxidized developer than are the corresponding tetraequivalent magenta couplers.

Examples of diequivalent magenta couplers are described in U.S. Pat. Nos. 3,006,579, 3,419,391, 3,311,476, 3,432,521, 3,214,437, 4,032,346, 3,701,783, 4,351,897, 3,227,554, in EP-A 133 503, DE-A 2 944 601, JP-A 78/34 044, 74/53 435, 74/53 436, 75/53 372 and 5/122 935.

Typical and preferred magenta couplers conform to the formulae:

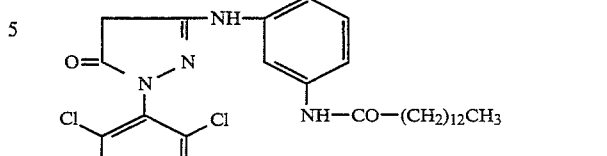

(M-1)

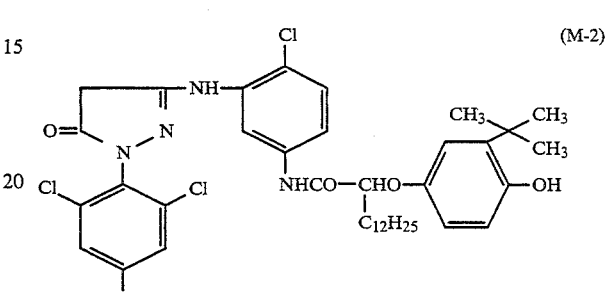

(M-2)

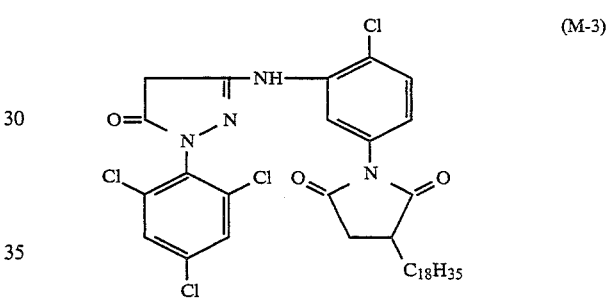

(M-3)

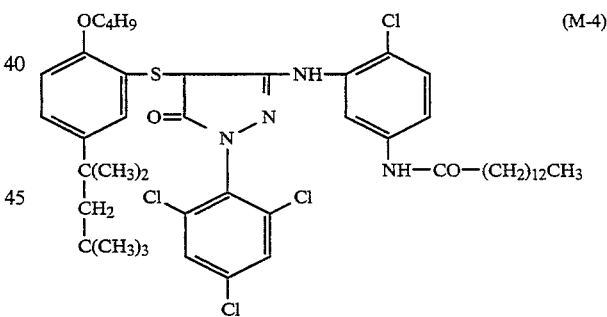

(M-4)

It is possible for 2 pyrazolone rings to be linked via a divalent Q', giving so-called bis-couplers. These are described, for example, in U.S. Pat. No. 2,632,702, U.S. Pat. No. 2,618,864, GB-A 968 461, GB-A 786 859, JP-A 76/37 646, 59/4086, 69/16 110, 69/26 589, 74/37 854 and 74/29 638. Y is preferably an O-alkoxyarylthio group.

As mentioned above, the magenta couplers used can also be pyrazoles fused to 5-membered heterocyclic rings, known as pyrazoloazoles. Their advantages over simple pyrazoles are that they give dyes of greater formalin resistance and have purer absorption spectra.

Magenta couplers of the pyrazoloazole type, which are likewise preferred, may be represented by the formula

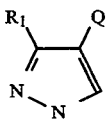 (C-2)

in which $R_1$ is hydrogen or a substituent, Z represents the non-metallic atoms necessary to complete a 5-membered ring containing 2 or 3 nitrogen atoms, it being possible for this ring to be substituted, and Q is hydrogen or a leaving group.

Of these compounds, preference is given to magenta couplers of the formulae

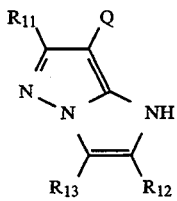 (C-3)

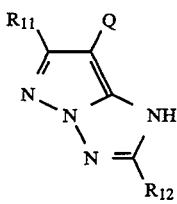 (C-4)

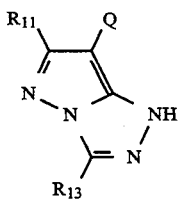 (C-5)

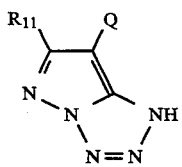 (C-6)

$R_{11}$, $R_{12}$ and $R_3$, independently of one another, are, for example, hydrogen, halogen, —$CR_3$ in which the radicals R, independently of one another, are hydrogen or alkyl, aryl, heterocyclyl, cyano, hydroxyl, nitro, carboxyl, amino, alkoxy, aryloxy, aeylamino, alkylamino, anilino, ureido, sulfamoylamino, alkylthio, arylthio, alkoxycarbonylamino, sulfonamido, carbamoyl, sulfamoyl, sulfonyl, alkoxycarbonyl, heterocyclyloxy, azo, acyloxy, carbamoyloxy, silyloxy, aryloxycarbonylamino, imido, heterocyclylthio, sulfinyl, phosphonyl, aryloxycarbonyl, acyl or azolyl, preferably hydrogen, halogen (for example chlorine or bromine), —$CR_3$ in which the radicals $R_3$, independently of one another, are hydrogen or alkyl, aralkyl, alkenyl, alkynyl, cycloalkyl or cycloalkenyl, particularly preferably methyl, ethyl, propyl, isopropyl, t-butyl, tridecyl, 2-methanesulfonylethyl, 3-(3-pentadecylphenoxy)propyl, 3-(4-(2-(4-(4-hydroxyphenylsulfonyl)phenoxy)dodecanamido)-phenyl)propyl, 2-ethoxytridecyl, trifluoromethyl, cyclopentyl, 3-(2,4-di-t-amylphenoxy)propyl; aryl (for example phenyl, 4-t-butylphenyl, 2,4-di-t-amylphenyl or 4-tetradecanamidophenyl); heterocyclyl (for example 2-furyl, 2-thienyl, 2-pyrimidinyl or 2-benzothiazolyl); cyano; hydroxyl, nitro; carboxyl; amino; alkoxy (for example methoxy, ethoxy, 2-methoxyethoxy; 2-dodecylethoxy, 2-methanesulfonylethoxy); aryloxy (for example phenoxy, 2-methylphenoxy, 4-t-butylphenoxy, 3-nitrophenoxy, 3-t-butyloxycarbamoylphenoxy or 3-methoxycarbamoyl); acylamino (for example acetamido, benzamido, tetradecanamido, 2-(2,4-di-t-amylphenoxy)butanamido, 4-(3-t-butyl-4-hydroxyphenoxy)-butanamido, 2-(4-(4-hydroxyphenylsulfonyl)phenoxy)-decanamido or methylbutylamino); anilino (for example phenylamino, 2-chloroanilino, 2-chloro-5-tetradecanaminoanilino, 2-chloro-5-dodecyloxycarbonylanilino, N-acetylanilino, 2-chloro-5-(alpha-(3-t-butyl-4-hydroxyphenoxy)dodecanamidoanilino); ureido (for example phenylureido, methylureido or N,N-dibutylureido); sulfamoylamino (for example N,N-dipropylsulfamoylamino or N-methyl-N-decylsulfamoylamino); alkylthio (for example methylthio, octylthio, tetradecylthio, 2-phenoxyethylthio, 3-phenoxypropylthio or 3-(4-t-butylphenoxy)propylthio); arylthio (for example phenylthio, 2-butoxy-5-t-octylphenylthio, 3-pentadecylphenylthio, 2-carboxyphenylthio or 4-tetradecanamidophenylthio); alkoxycarbonylamino (for example methoxycarbonylamino or tetradecyloxycarbonylamino); sulfonamido (for example methanesulfonamido, hexadecanesulfonamido, benzenesulfonamido, p-toluenesulfonamido, octadecanesulfonamido or 2-methoxy-5-t-butylbenzenesulfonamido); carbamoyl (for example N-ethylcarbamoyl, N,N-di-butylcarbamoyl, N-(2-dodecyloxyethyl)carbamoyl, N-methyl-N-dodecylcarbamoyl or N-(3-(2,4-di-t-amylphenoxy)-propyl)carbamoyl); sulfamoyl (for example N-ethyl-sulfamoyl, N,N-dipropylsulfamoyl, N-2-(dodecyloxyethyl)sulfamoyl, N-ethyl-N-dodecylsulfamoyl or N,N-diethylsulfamoyl); sulfonyl (for example methanesulfonyl, octanesulfonyl, benzenesulfonyl or toluenesulfonyl); alkoxycarbonyl (for example methoxycarbonyl, butoxycarbonyl, dodecyloxycarbonyl or octadecyloxycarbonyl); heterocyclyloxy (for example 1-phenyltetrazol-5-oxy or 2-tetrahydropyranyloxy); azo (for example phenylazo, 4-methoxyphenylazo, 4-pivaloylaminophenylazo or 2-hydroxy-4-propanoylphenylazo); acyloxy (for example acetoxy); carbamoyloxy (for example N-methylcarbamoyloxy or N-phenylcarbamoyloxy); silyloxy (for example trimethylsilyloxy or dibutylmethylsilyloxy); aryloxycarbonylamino (for example phenoxycarbonylamino); imido (for example N-succinimido, N-phthalimido or 3-octadecenylsuccinimido); heterocyclylthio (for example 2-benzothiazolylthio, 2,4-diphenyloxy-1,3,5-triazole-6-thio or 2-pyridylthio); sulfinyl (for example dodecanesulfinyl, 3-pentadecylphenylsulfinyl or 3-phenoxypropylsulfinyl); phosphonyl (for example phenoxyphosphonyl, octyloxyphosphonyl or phenylphosphonyl); aryloxycarbonyl (for example phenoxycarbonyl); acyl (for example acetyl, 3-phenylpropanoyl, benzoyl or 4-dodecyloxybenzoyl); or azolyl (for example imidazolyl, pyrazolyl or 3-chloropyrazol-1-yl).

These substituents may be further substituted, for example by halogen or by an organic radical bonded via a C, O, N or S atom.

Preferred groups $R_{11}$ are alkyl, aryl, alkoxy, aryloxy, alkylthio, ureido, urethane and acylamino groups.

$R_{12}$ may be as defined for $R_{11}$ and is preferably hydrogen, alkyl, aryl, a heterocyclic ring, alkoxycarbonyl, carbamoyl, sulfamoyl, sulfinyl, acyl or cyano.

$R_{13}$ may be as defined for $R_{11}$ and is preferably hydrogen, alkyl, aryl, a heterocyclic ring, alkoxy, aryloxy, alkylthio, arylthio, alkoxycarbonyl, carbamoyl or acyl, in particular alkyl, aryl, a heterocyclic ting, alkylthio or arylthio.

Q is hydrogen or a leaving group, such as halogen, alkoxy, aryloxy, acyloxy, alkyl- or arylsulfonyloxy, acylamino, alkyl- or arylsulfonamido, alkoxycarbonyloxy, aryloxycarbonyloxy, alkyl-, aryl- or heterocyclyl-S-carbamoylamino, a 5- or 6-membered, nitrogen-containing heterocyclic radical, imido or arylazo. These groups may be further substituted as indicated for $R_{11}$.

Q is preferably halogen (for example fluorine, chlorine or bromine); alkoxy (for example ethoxy, dodecyloxy, methoxyethylcarbamoylmethoxy, carboxypropoxy, methylsulfonylethoxy or ethoxycarbonylmethoxy); aryloxy (for example 4-methylphenoxy, 4-chlorophenoxy, 4-methoxyphenoxy, 4-carboxyphenoxy, 3-ethoxycarboxyphenoxy, 3-acetylaminophenoxy or 2-carboxyphenoxy); acyloxy (for example acetoxy, tetradecanoyloxy or benzoyloxy); alkyl- or arylsulfonyloxy (for example methanesulfonyloxy or toluenesulfonyloxy); acylamino (for example dichloroacetylamino or heptafluorobutyrylamino); alkyl- or arylsulfonamido (for example methanesulfonamido, trifluoromethanesulfonamido or p-toluenesulfonamido); alkoxycarbonyloxy (for example ethoxycarbonyloxy or benzyloxycarbonyloxy); aryloxycarbonyloxy (for example phenoxycarbonyloxy); alkyl-, aryl- or heterocyclyl-S- (for example dodecylthio, 1-carboxydodecylthio, phenylthio, 2-butoxy-5-t-octylphenylthio or tetrazolylthio); carbamoylamino (for example N-methylcarbamoylamino or N-phenylcarbamoylamino); a 5- or 6-membered, nitrogen-containing ring (for example imidazolyl, pyrazolyl, triazolyl, tetrazolyl or 1,2-dihydro-2-oxo-1-pyridyl); imido (for example succinimido or hydantoinyl); or arylazo (for example phenylazo or 4-methoxyphenylazo).

Q may alternatively form corresponding bis-compounds by condensation of 4 equivalents of coupler with an aldehyde or ketone. Furthermore, Q may contain photographically active groups, such as development inhibitors or development accelerators. Q is preferably halogen, alkoxy, aryloxy, alkyl- or arylthio, or a 5- or 6-membered, nitrogen-containing, heterocyclic group which is bonded to the coupling site via a nitrogen atom.

Pyrazolotetrazoles are described in JP-A 85/33 552; pyrazolopyrazoles in JP-A 85/43 695; pyrazoloimidazoles in JP-A 85/35 732, JP-A 86/18 949 and U.S. Pat. No. 4 500 630; pyrazolotriazoles in JP-A 85/186 567, JP-A 86/47 957, JP-A 85/215 687, JP-A 85/197 688, JP-A 85/172 982, EP-A 119 860, EP-A 173 256, EP-A 178 789, EP-A 178 788 and in Research Disclosure 84/24 624.

Further pyrazoloazole magenta couplers are described in: JP-A 86/28 947, JP-A 85/140 241, JP-A 85/262 160, JP-A 85/213 937, JP-A 87/278 552, JP-A 87/279 340, JP-A 88/100 457, EP-A 177 765, EP-A 176 804, EP-A 170 164, EP-A 164 130, EP-A 178 794, DE-A 3 516 996, DE-A 3 508 766 and Research Disclosure 81/20 919, 84/24 531 and 85/25 758.

Examples of suitable couplers of this type are:

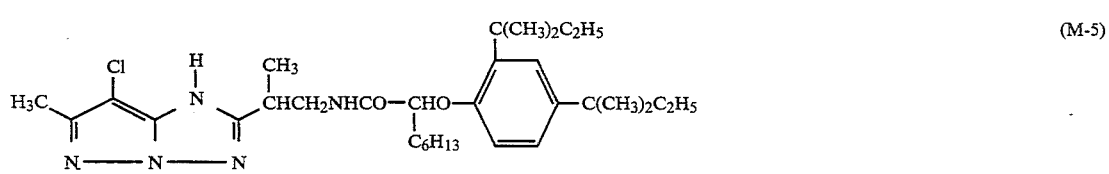

(M-5)

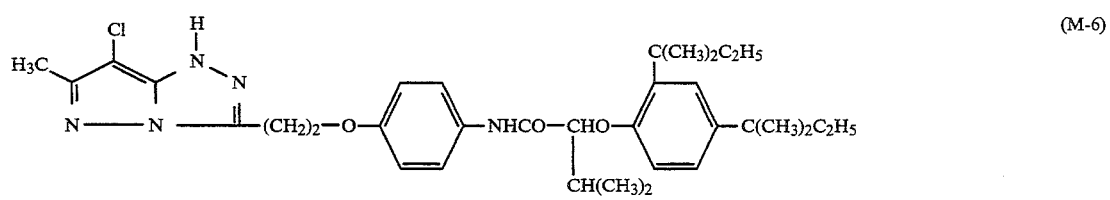

(M-6)

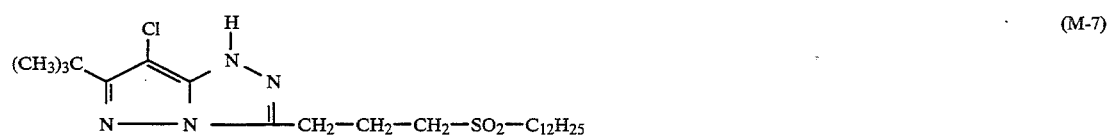

(M-7)

(M-8)

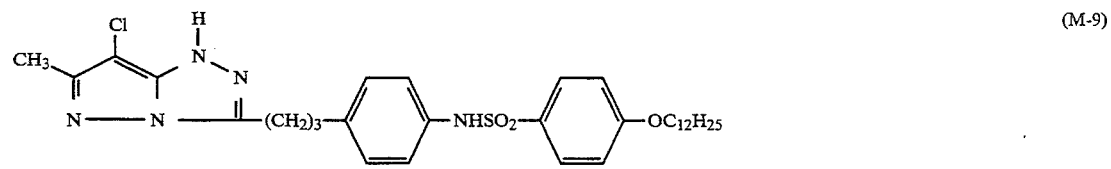

(M-9)

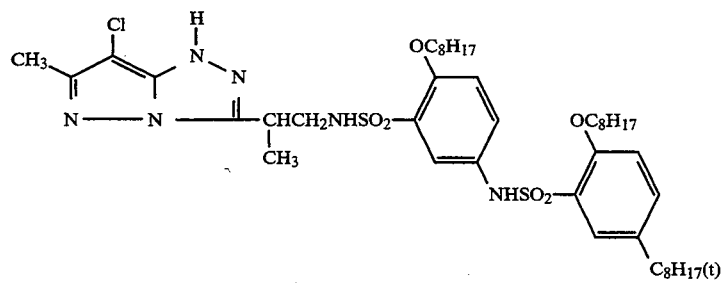
(M-10)
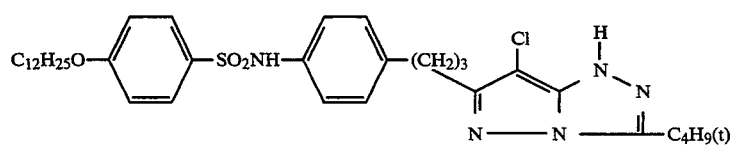
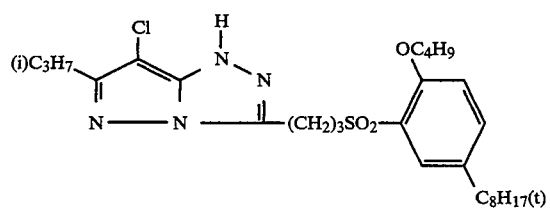
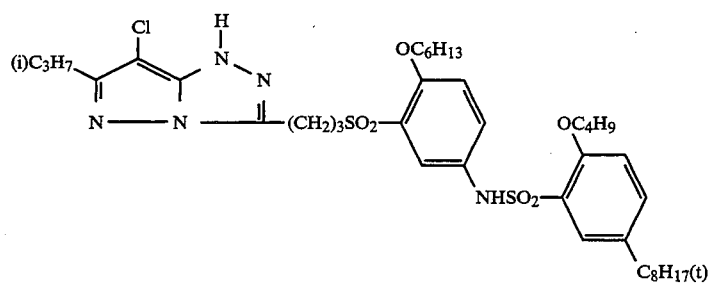
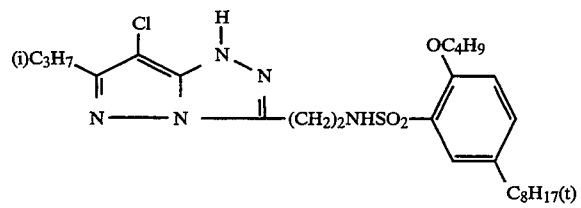
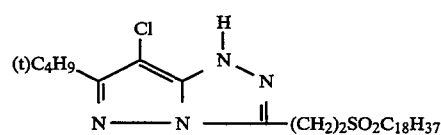
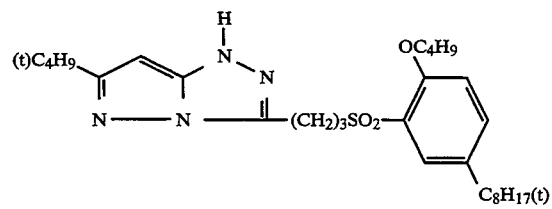

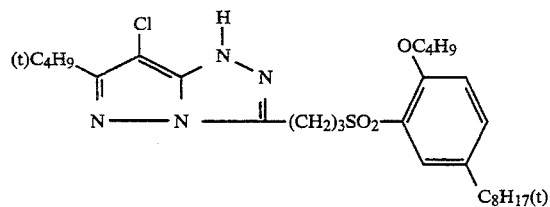
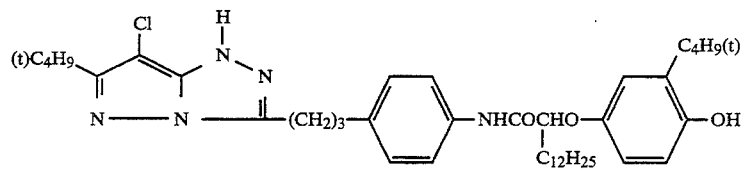
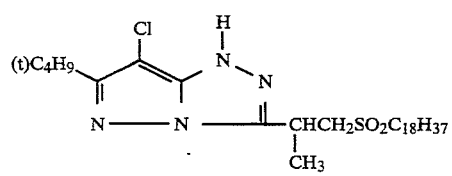
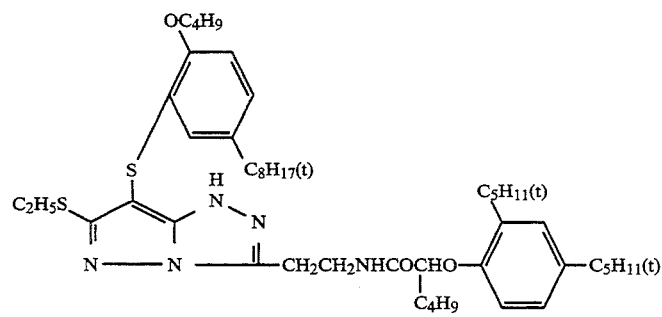
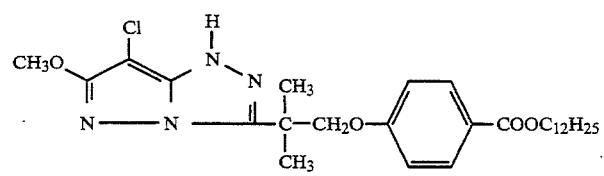
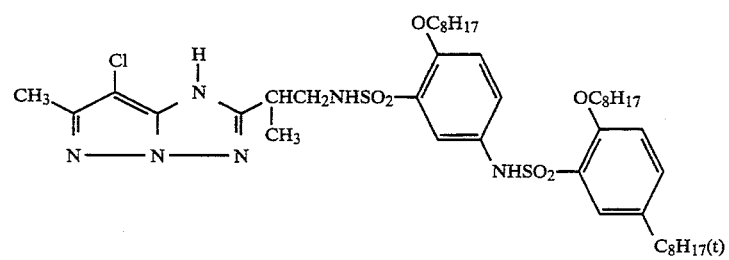
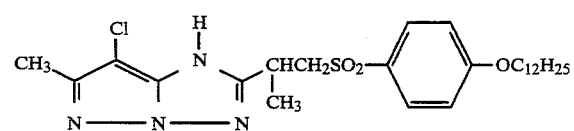
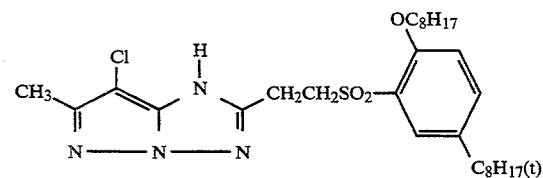

-continued
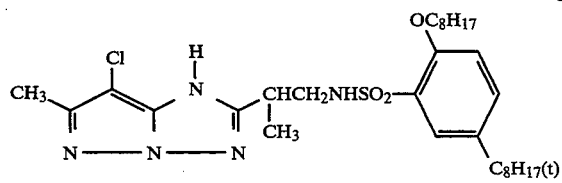
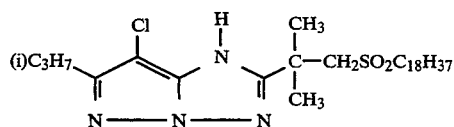
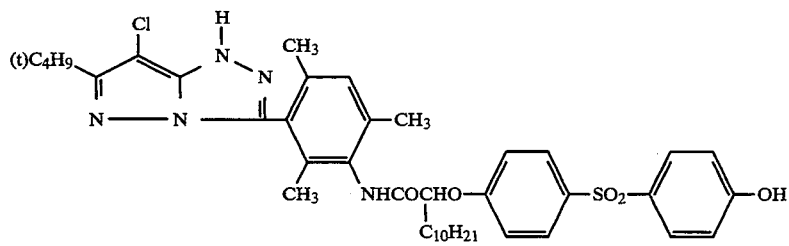
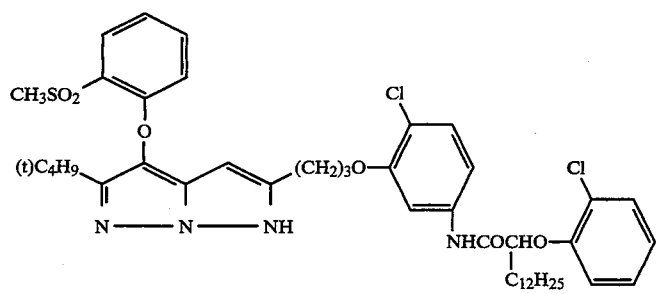
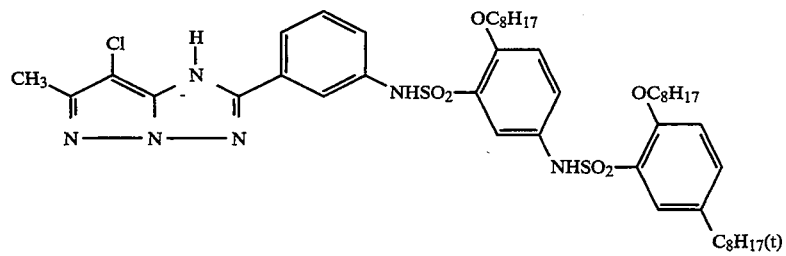
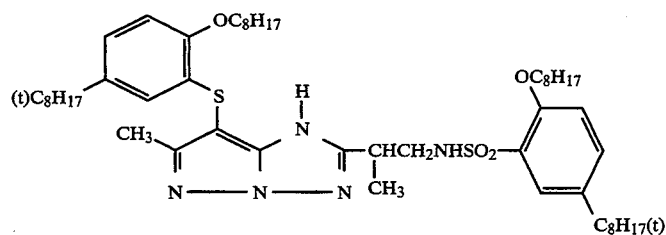
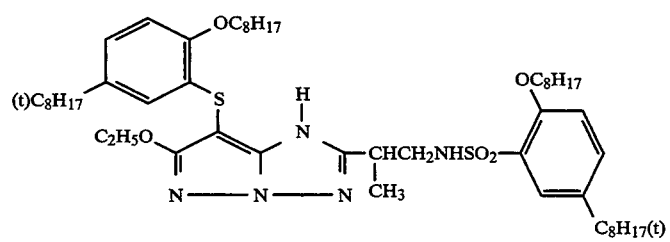

-continued
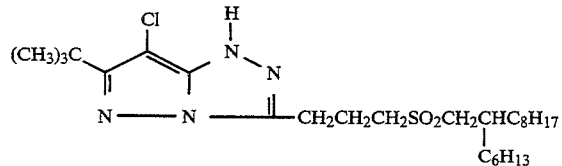
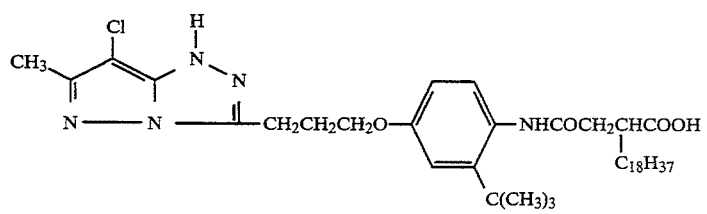
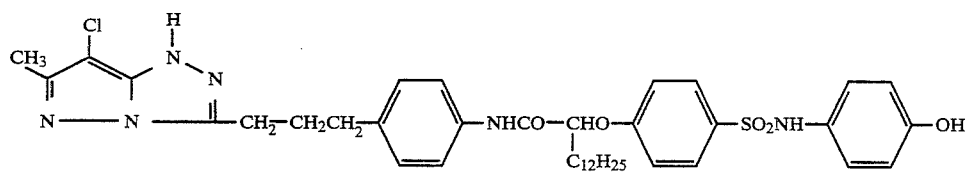
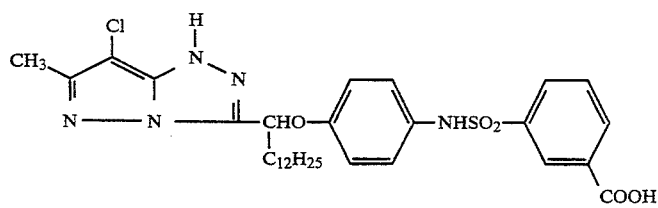
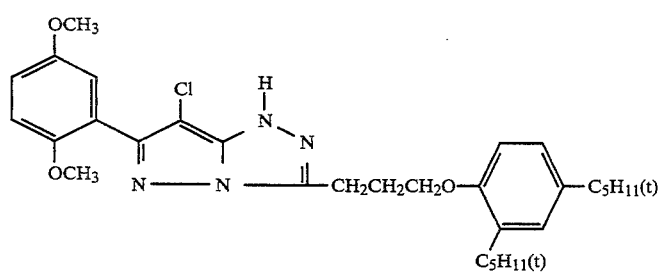
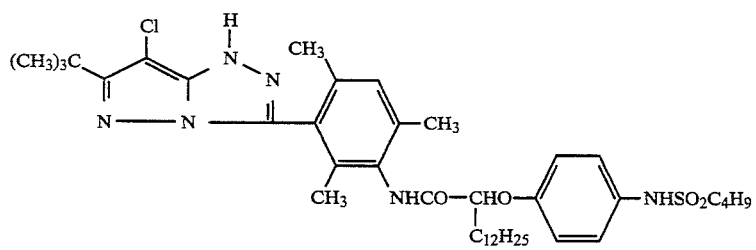
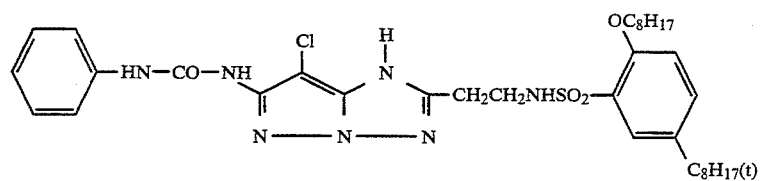
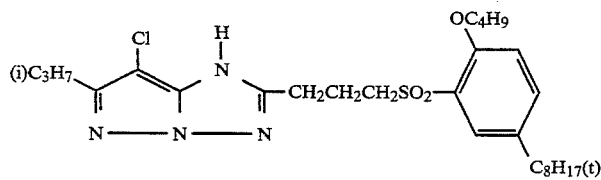

-continued
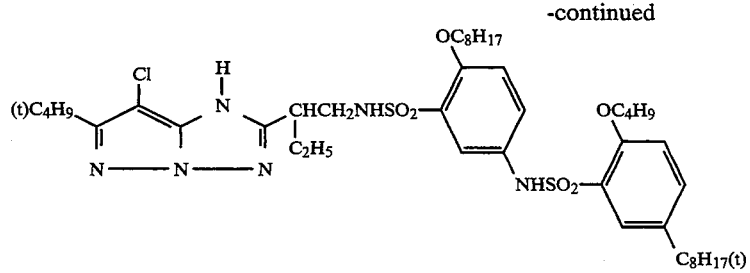
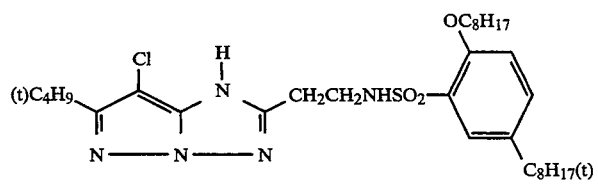
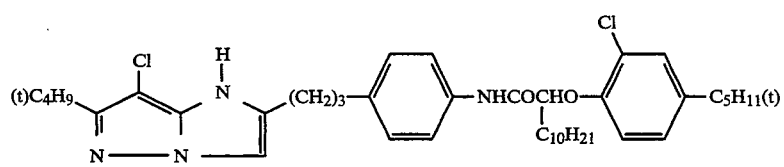
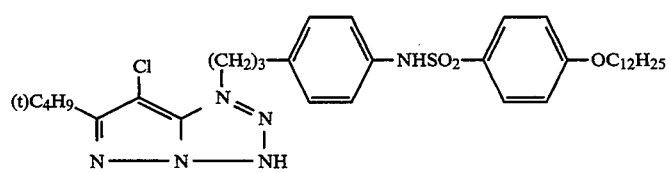
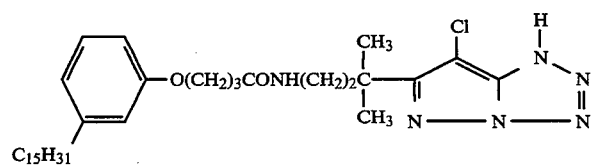
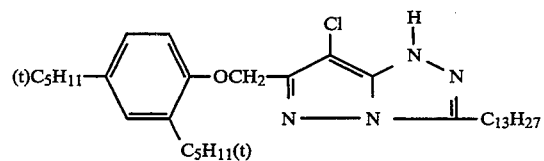
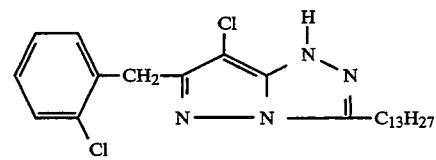
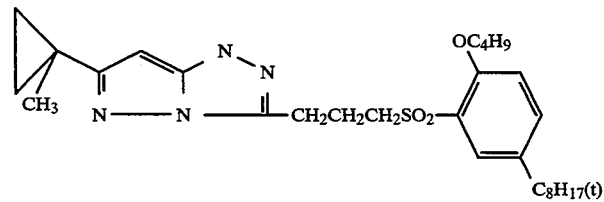
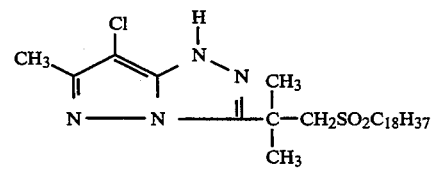

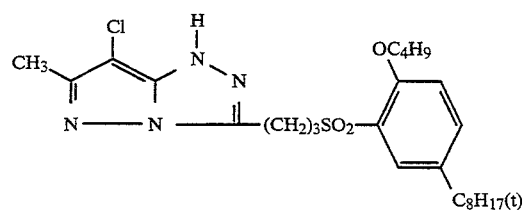
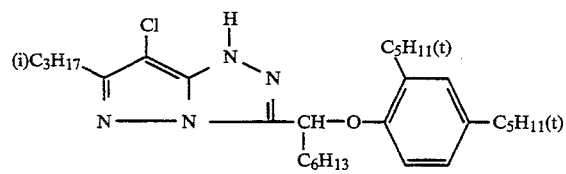
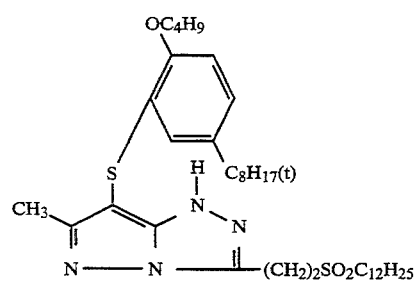
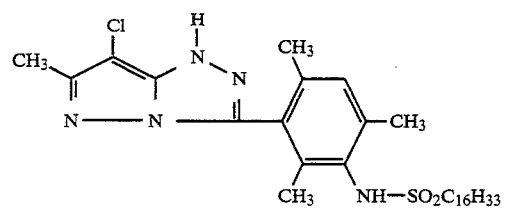
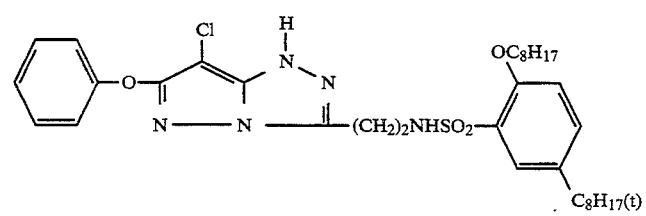
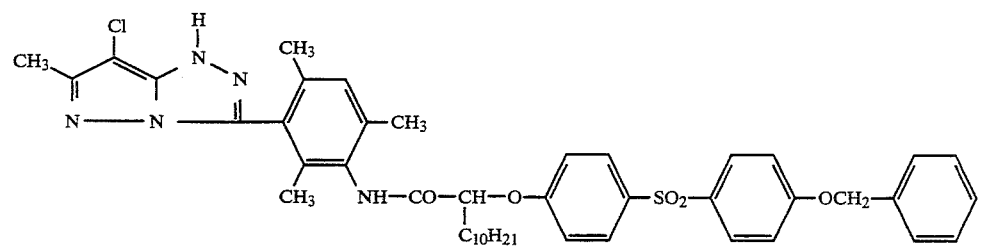
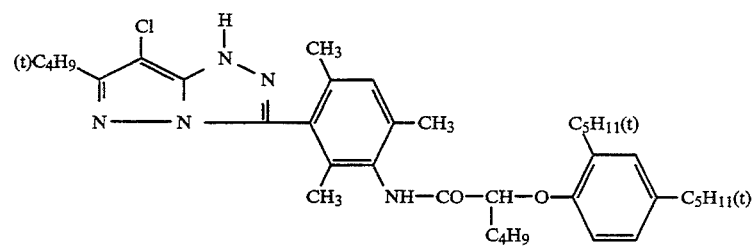

-continued
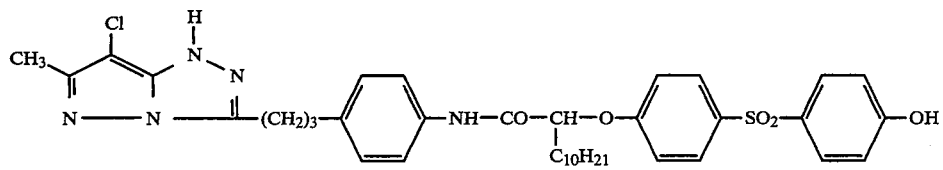
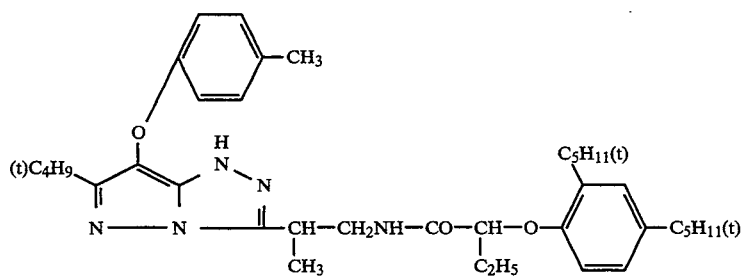
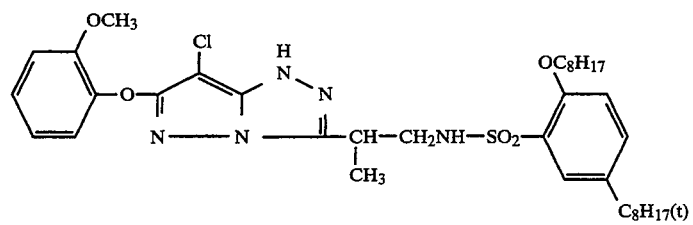
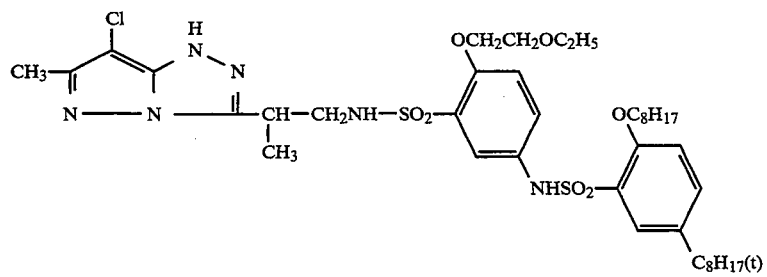
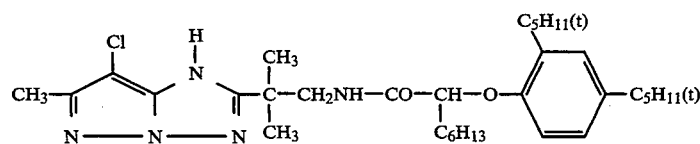
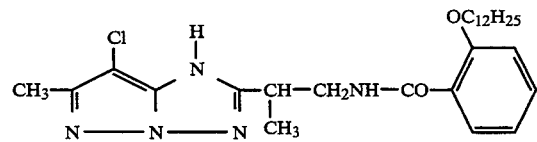
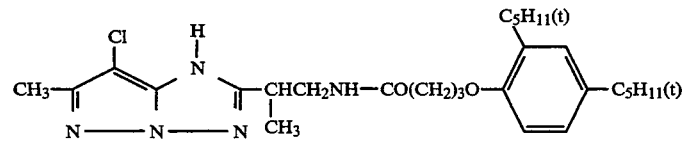
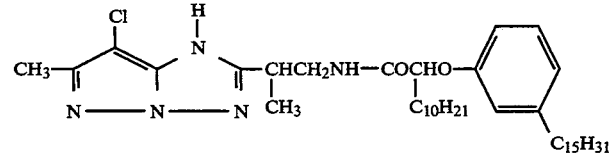

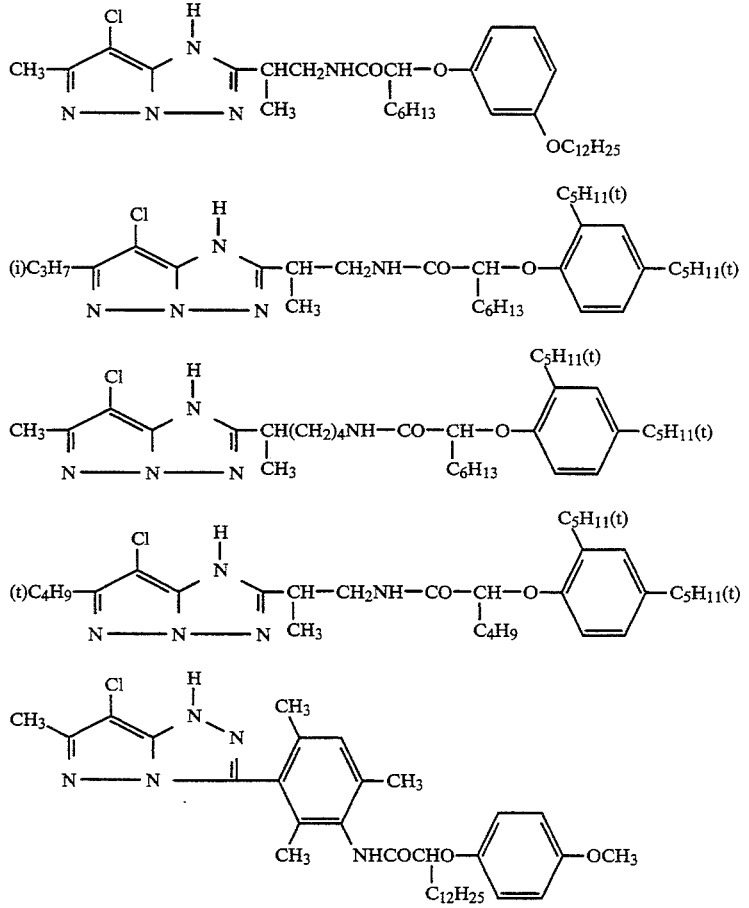

Yellow couplers which can be used in the material according to the invention are preferably compounds of the formula A $$R_1-CO-\overset{Q}{\underset{|}{C}H}-CO-NHR_2, \quad (A)$$

in which $R_1$ is alkyl or aryl, $R_2$ is aryl and Q is hydrogen or a group which can be eliminated by reaction with the oxidized developer.

A group of yellow couplers comprises the compounds of the formula A in which $R_1$ is t-butyl and $R_2$ is a group of the formula

in which $R_3$ is hydrogen, halogen, alkyl or alkoxy, and $R_4$, $R_5$ and $R_6$ are hydrogen, halogen, alkyl, alkenyl, alkoxy, aryl, carboxyl, alkoxycarbonyl, carbamoyl, sulfonyl, sulfamoyl, alkylsulfonsulfonamamido, acylamino, ureido or amino.

Preferably, $R_3$ is chlorine, $R_4$ and $R_5$ are hydrogen and $R_6$ is an acylamino group. This group also includes the compounds of the formula

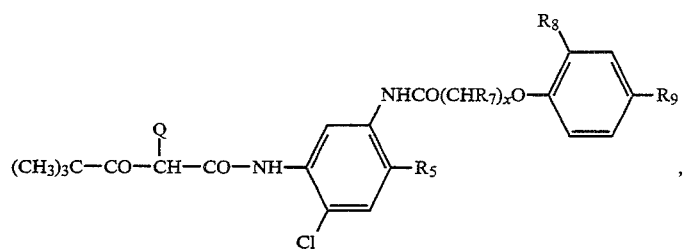

in which x is 0–4, $R_7$ is hydrogen or alkyl, and $R_8$ and $R_9$ are alkyl.

Another group of yellow couplers conforms to the formula B

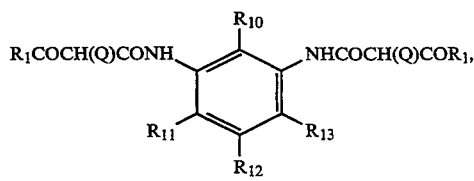

in which $R_{10}$ is hydrogen, halogen or alkoxy, $R_{11}$, $R_{12}$ and $R_{13}$ are hydrogen, halogen, alkyl, alkenyl, alkoxy, aryl, carboxyl, alkoxycarbonyl, carbamoyl, sulfonyl, sulfamoyl, sulfonamido, acylamino, ureido or amino, and $R_1$ and Q are as defined above.

This group includes compounds of the formula B in which $R_1$ is t-butyl, $R_{10}$ is chlorine, $R_{11}$ and $R_{13}$ are hydrogen, and $R_{12}$ is alkoxycarbonyl.

In the compounds of the formulae A and B, leaving group Q may be hydrogen or a heterocyclic group

in which $R_{14}$ is a divalent organic group which supplements the ring to make up a 4–7-membered ring, or Q is an —$OR_{15}$ group in which $R_{15}$ is alkyl, aryl, acyl or a heterocyclic radical.

Typical examples of customary yellow couplers are the compounds of the formulae below:

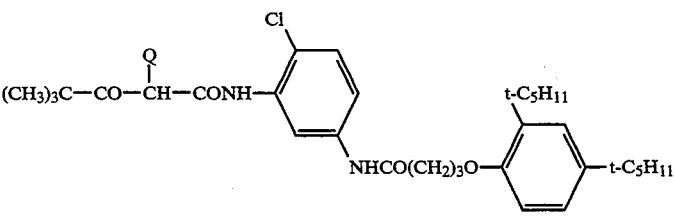

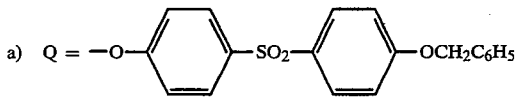

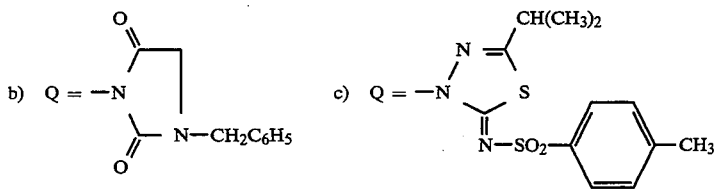

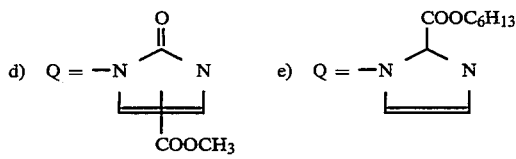

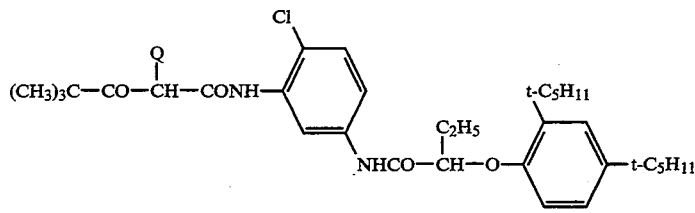

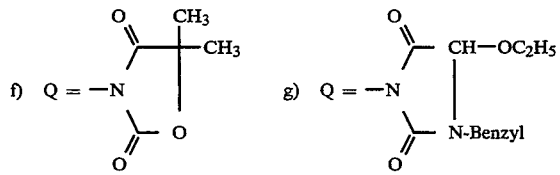

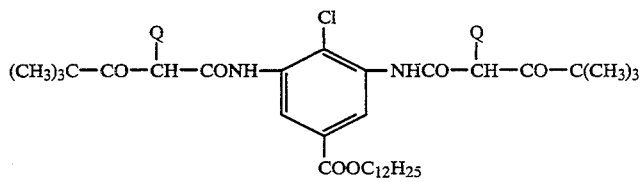
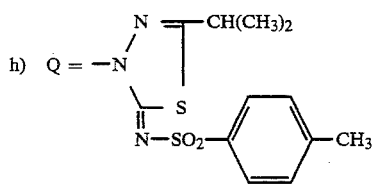
Further examples of yellow couplers are given in U.S. Pat. Nos. 2,407,210, 2,778,658, 2,875,057, 2 908,513, 2,908,573, 3,227,155, 3,227,550, 3,253,924, 3,265,506, 3,277,155, 3,408,194, 3,341,331, 3,369,895, 3,384,657, 3,415,652, 3,447,928, 3,551,155, 3,582,322, 3,725,072, 3,891,445, 3,933,501, 4,115,121, 4,401,752 and 4,022,620, in DE-A 1 547 868, 2,057,941, 2,162,899, 2,163,813, 2,213,461, 2,219,917, 2,261,361, 2,261,362, 2,263,875, 2,329,587, 2,414,006 and 2,422,812, in GB-A 1 425 020 and 1 077 874 and in JP-A 88/123 047 and in EP-A 447 969.
Typical and preferred yellow couplers conform to the formulae:
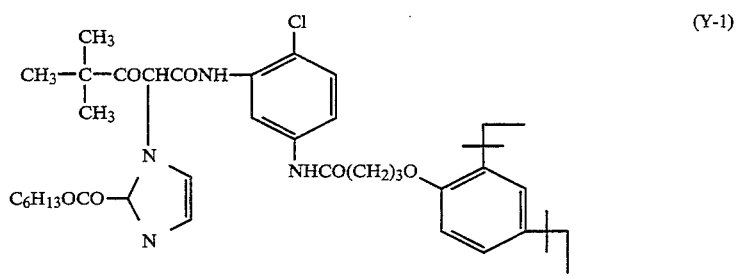
(Y-1)
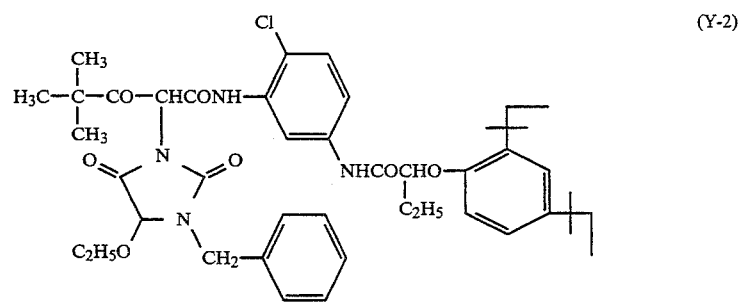
(Y-2)
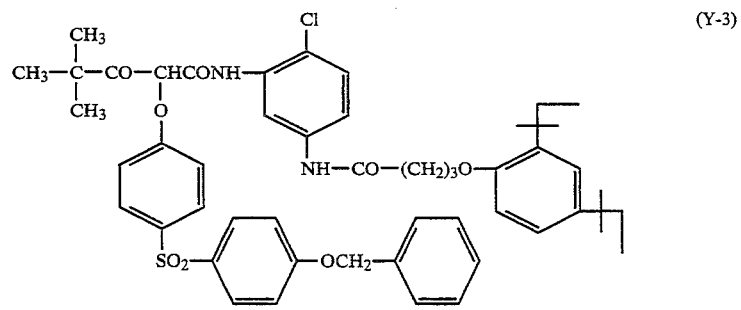
(Y-3)

-continued
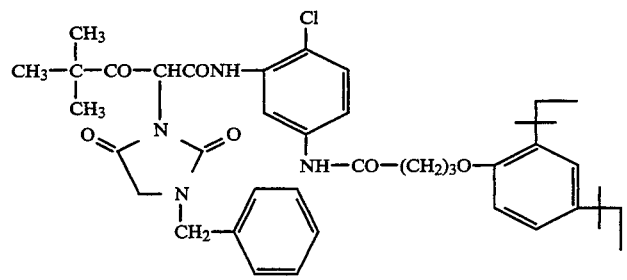 (Y-4)
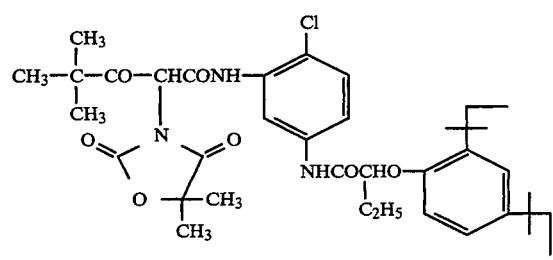 (Y-5)
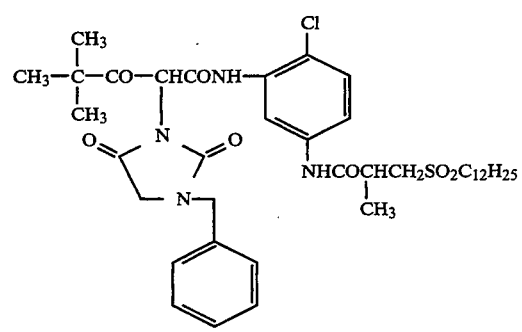 (Y-6)
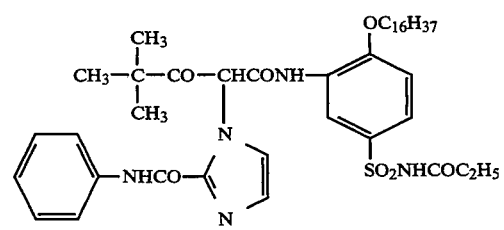 (Y-7)
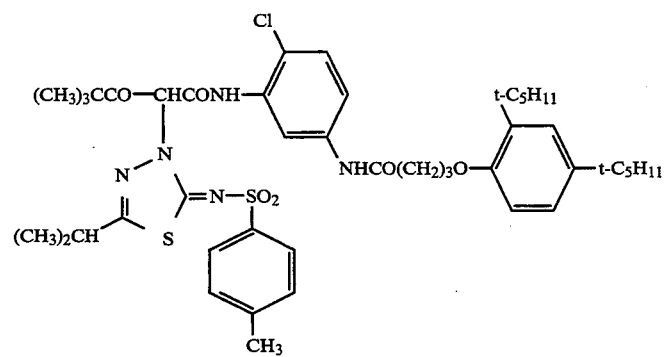 (Y-8)

-continued

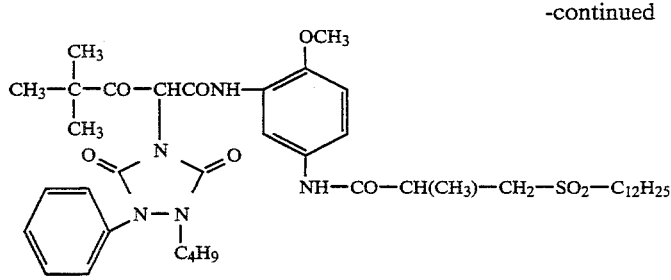
(Y-9)

Cyan couplers may be, for example, derivatives of phenol, of 1-naphthol or of pyrazoloquinazolone. Preference is given to structures of the formula E

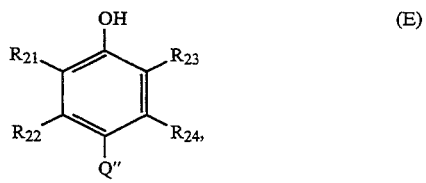
(E)

in which $R_{21}$, $R_{22}$, $R_{23}$ and $R_{24}$ are hydrogen, halogen, alkyl, carbamoyl, amino, sulfonamido, phosphoramido or ureido. $R_{21}$ is preferably H or Cl, $R_{22}$ is preferably an alkyl or amino group, $R_{23}$ is preferably an amino group and $R_{24}$ is preferably hydrogen. Q'' is hydrogen or a leaving group which is eliminated during the reaction with the oxidized developer. A detailed list of cyan couplers is given in U.S. Pat. No. 4,456,681.

Further examples of cyan couplers are given in the following: U.S. Pat. Nos. 2,369,929, 2,423,730, 2,434,272, 2,474,293, 2,521,293, 2,521,908, 2,698,794, 2,706,684, 2,772,162, 2,801,171, 2,895,826, 2,908,573, 3,034,892, 3,046,129, 3,227,550, 3,253,294, 3,311,476, 3,386,301, 3,419,390, 3,458,315, 3,476,560, 3,476,563, 3,516,831, 3,560,212, 3,582,322, 3,583,971, 3,591,383, 3,619,196, 3,632,347, 3,652,286, 3,737,326, 3,758,308, 3,839,044, 3,880,661, 4,004,929, 4,124,396, 4,333,999, 4,463,086, 4,456,681, 4,873,183 and 4,923,791 and in EP-A 354 549 and EP-A 398 664.

The red-sensitive silver-halide emulsion layer of the material according to the invention preferably contains a cyan coupler of the formula

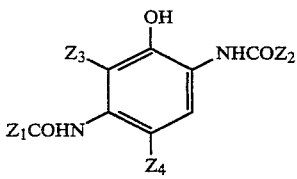
(E-1)

and/or of the formula

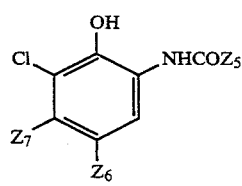
(E-2)

in which $Z_1$ is alkyl or aryl, $Z_2$ is alkyl, cycloalkyl, aryl, a heterocyclic group or a ballast group, $Z_3$ is hydrogen or halogen, Z1 and Z3 together can form a ring, and $Z_4$ is hydrogen or a leaving group, and $Z_5$ is a ballast group, $Z_6$ is hydrogen or a leaving group and $Z_7$ is alkyl.

Examples of customary cyan couplers are the following:

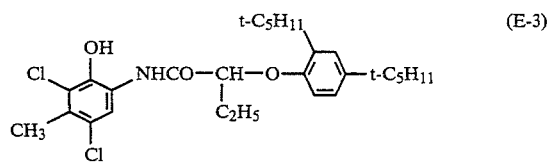
(E-3)

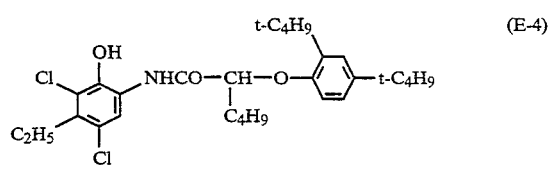
(E-4)

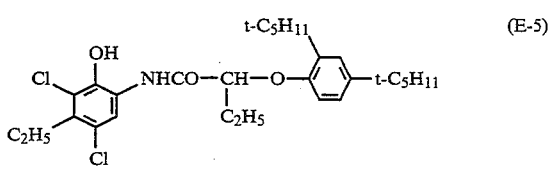
(E-5)

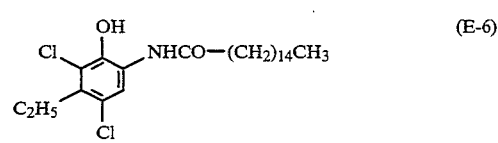
(E-6)

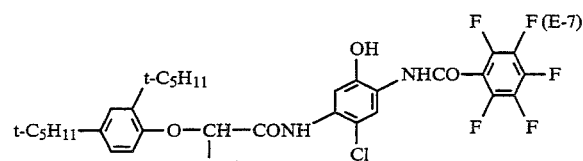
(E-7)

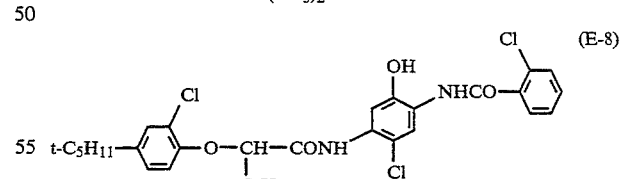
(E-8)

The colour developers usually used for colour-photographic materials are p-dialkylaminoanilines. Examples of these are 4-amino-N,N-diethylaniline, 3-methyl-4-amino-N,N-diethylaniline, 4-amino-N-ethyl-N-α-hydroxyethylaniline, 3-methyl-4-amino-N-ethyl-N-α-hydroxyethylaniline, 3-methyl-4-amino-N-ethyl-N-α-methanesulfonamidoethylaniline, 3-methyl-4-amino-N-ethyl-N-α-methoxyethylaniline, 3-α-methanesulfonamidoethyl-4-amino-N,N-diethylaniline, 3-methoxy-4-amino-N-ethyl-N-α-hydroxyethylaniline, 3methoxy- 4-amino-N-ethyl-N-α-methoxyethylaniline, 3-acetamido-4-amino-N,N-diethylaniline, 4-amino-N,N-dimethylaniline, N-ethyl-N-α-[α'-(α''-methoxyethoxy)ethoxy]ethyl-3-methyl-4-aminoaniline, N-ethyl-N-α-(α'-methoxyethoxy)ethyl-3-methyl-4-aminoaniline, and the salts of these compounds, for example sulfates, hydrochlorides or toluenesulfonates.

The compounds of the formulae (I), (II), (III) and (IV) according to the invention, the magenta couplers and other colour couplers can be incorporated into the colour-photographic material in a known manner, for example into silver, halide emulsions which contain gelatin and/or other binders. They are used, for example, in silver-bromide, silver-chloride or silver-iodide emulsions or in emulsions which contain mixtures of silver halides, such as silver bromide/iodide or silver-chloride/bromide emulsions.

The compounds of the formulae (I), (II), (III) and (IV) according to the invention can be incorporated into the colour-photographic material together with the magenta coupler and if desired further additives by predissolving them in high-boiling organic solvents. Preference is given to solvents which boil higher than 160° C. Typical examples of these solvents are the esters of phthalic acid, phosphoric acid, citric acid, benzoic acid or fatty acids, and alkylamides and phenols.

A low-boiling solvent is usually used in addition in order to simplify incorporation of the additives into the colour-photographic material. Examples of such solvents are esters, for example ethyl acetate, alcohols, for example butanol, ketones, for example methyl isobutyl ketone, chlorinated hydrocarbons, for example methylene chloride, and amides, for example dimethylformamide. If the additives are themselves liquid, they can also be incorporated into the photographic material without the assistance of solvents.

The compounds according to the invention may if desired be dispersed in the gelatin layer as oil.

Further details on high-boiling solvents which can be used are given in the publications below:

Phosphates: GB-A 791 219, BE-A 755 248, JP-A 76/76 739, 78/27 449, 78/218 252, 78/97 573, 79/148 133, 82/216 177, 82/93 323 and 83/216 177 and EP-A 265 296.

Phthalates: GB-A 791 219, JP-A 77/98 050, 82/93 322, 82/216 176, 82/218 251, 83/24 321, 83/45 699 and 84/79 888.

Amides: GB-A 791 129, JP-A 76/105 043, 77/13 600, 77/61 089, 84/189 556, 87/239 149, EP-A 270 341 and WO 88/00 723.

Phenols: GB-A 820 329, FR-A 1 220 657, JP-A 69/69 946, 70/3 818, 75/123 026, 75/82 078, 78/17 914, 78/21 166, 82/212 114 and 83/45 699.

Other oxygen-containing compounds: U.S. Pat. Nos. 3,748,141, 3,779,765, JP-A 73/75 126, 74/101 114, 74/10 115, 75/101 625, 76/76 740, 77/61 089, EP-A 304 810 and BE-A 826 039.

Other compounds: JP-A 72/115 369, 72/130 258, 73/127 521, 73/76 592, 77/13 193, 77/36 294, 79/95 233, 91/2748, 193/105 147 and Research Disclosure 82/21 918.

The amount of high-boiling solvent is, for example, in the range from 50 mg to 2 g per m² of base, preferably from 200 mg to 1 g per m².

The photographic layers may furthermore contain colour cast inhibitors. These prevent colour casts being formed, due, for example, to reaction of the coupler with unintentionally oxidized developer or with by-products of the colour-formation process. Colour cast inhibitors of this type are usually hydroquinine derivatives, but may also be derivatives of aminophenols, of gallic acid or of ascorbic acid. Typical examples of these inhibitors are given in the publications below: U.S. Pat. Nos. 2,360,290, 2,336,327, 2,403,721, 2,418,613, 2,675,314, 2,701,197, 2,704,713, 2,728,659, 2,732,300, 2,735,365; EP-A 124 877, EP-A 277 589, EP-A 338 785; JP-A 75/92 988, 75/92 989, 75/93 928, 75/110 337, 84/5 247 and 77/146 235.

Photographic layers may also contain DIR couplers (DIR denotes Development Inhibition Release), which form colourless compounds with the oxidized developer. They are added to improve the sharpness and grain of the colour prints.

The photographic layers in the material according to the invention may also contain UV absorbers. These filter out the UV light and thus protect the dyes, the couplers and other components against photodegradation. Examples of such UV absorbers are 2-(2-hydroxyphenyl)benzotriazoles, 2-hydroxyphenyl-1,3,5-triazines, 2-hydroxybenzophenones, salicylic acid esters, acrylonitrile derivatives or thiazolines. UV absorbers of this type are described in greater detail, for example, in the following publications: U.S. Pat. Nos. 3,314,794, 3,352,681, 3,705,805, 3,707,375, 4,045,229, 3,700,455, 3,533,794, 3,698,907, 3,705,805, 3,738,837 and JP-A 71/2784. Preferred UV absorbers are the 2-(2-hydroxyphenyl)benzotriazoles (HBTs) of the formula

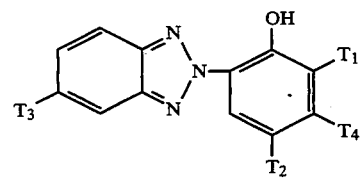

in which $T_1$, $T_2$ and $T_3$, independently of one another, are hydrogen, halogen, alkyl, alkyl which is substituted by a carboxylate group, alkoxy, aryloxy, hydroxyl or acyloxy, and $T_4$ is hydrogen, alkoxy, aryloxy or acyloxy.

Particular preference is given to HBT compounds which are liquid at room temperature.

Examples of preferred HBT compounds are:

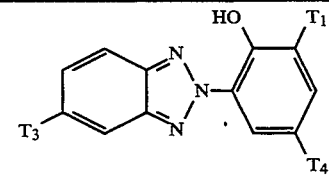

| HBT No. | $T_1$ | $T_4$ | $T_3$ |
|---|---|---|---|
| HBT-1 | H | $CH_3$ | H |
| HBT-2 | H | $C(CH_3)_3$ | H |
| HBT-3 | $C(CH_3)_3$ | $CH_3$ | Cl |
| HBT-4 | $C(CH_3)_3$ | $C(CH_3)_3$ | Cl |
| HBT-5 | $C(CH_3)_2C_2H_5$ | $C(CH_3)_2C_2H_5$ | H |
| HBT-6 | $CH(CH_3)C_2H_5$ | $C(CH_3)_3$ | H |
| HBT-7 | $C(CH_3)_2$—⌬ | $C(CH_3)_2$—⌬ | H |
| HBT-8 | $C(CH_3)_3$ | $CH_2CH_2COOC_8H_{17}$ | Cl |

-continued

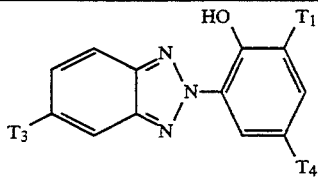

| HBT No. | T₁ | T₄ | T₃ |
|---|---|---|---|
| HBT-9 | C(CH₃)₃ | (isomers)<br>CH₂CH₂COOC₈H₁₇ | H |
| HBT-10 | C₁₂H₂₅ (isomers)* | (isomers)<br>CH₃ | H |

*Principal product

Other preferred UV absorbers are 2-hydroxyphenyl-1,3,5-triazines of the formula

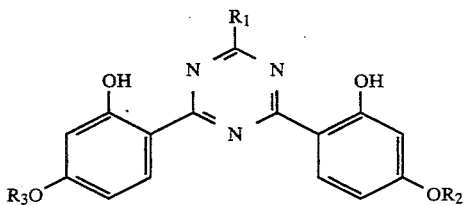

in which $R_1$ is a group of the formula

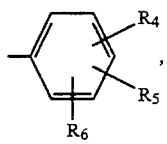

where $R_4$, $R_5$ and $R_6$, independently of one another, are hydrogen, $C_1-C_{12}$alkyl or halogen, or $R_1$ is a group of the formula

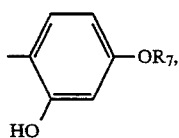

and $R_2$, $R_3$ and $R_7$, independently of one another, are monovalent organic radicals. $R_2$, $R_3$ and $R_7$ are preferably, independently of one another, a radical CH₂CH(OR₈)CH₂OR₉, where $R_8$ is hydrogen or acetyl, and $R_9$ is $C_1-C_4$alkyl ist.

The photographic layers may also contain phenolic Compounds which act as light stabilizers for the colour image and as colour cast inhibitors. They may be present in a light-sensitive layer (colour layer) or in an intermediate layer, alone or together with other additives. Such compounds are described in greater detail, for example, in the publications below: U.S. Pat. Nos. 3,700,455, 3,591,381, 3,573,052, 4,030,931, 4,174,220, 4,178,184, 4,228,235, 4,279,990, 4,346,165, 4,366,226, 4,447,523, 4,528,264, 4,581,326, 4,562,146, 4,559,297, GB-A 1 309 277, 1 547 302, 2 023 862, 2 135 788, 2 139 370, 2 156 091; DE-A 2 301 060, 2 347 708, 2 526 468, 2 621 203, 3 323 448; DD-A 200 691,214 468; EP-A 106 799, 113 124, 125 522, 159 912, 161 577, 164 030, 167 762, 176 845, 246 766, 320,776; JP-A 74/134 326, 76/127 730, 76/30 462, 77/3 822, 77/154 632, 78/10 842, 79/48 535, 79/70 830, 79/73 032, 79/147 038, 79/154 325, 79/155 836, 82/142 638, 83/224 353, 84/5246, 84/72 443, 84/87 456, 84/192 246, 84/192 247, 84/204 039, 84/204 040, 84/212 837, 84/220 733, 84/222 836, 84/228 249, 86/2540, 86/8843, 86/18 835, 86/18 836, 87/11 456, 87/42 245, 87/62 157, 86/6652, 89/137 258 and in Research Disclosure 79/17 804.

The photographic layers may also contain certain phosphorus(III) compounds, in particular phosphites and phosphonites. These act as light stabilizers for the colour images and as dark-storage stabilizers for magenta couplers. They are preferably added to the high-boiling solvents together with the coupler. Phosphorus-(III) compounds of this type are described in greater detail, for example, in the publications below: U.S. Pat. No. 4,407,935, U.S. Pat. No. 4,436,811, U.S. Pat. No. 4,956,406, EP-A 181 289, JP-A 73/32 728, JP-A 76/1420 and JP-A 55/66 741.

The photographic layers may also contain organometallic complexes which are light stabilizers for the colour images, in particular for the magenta dyes. Such compounds and combinations thereof with other additives are described in greater detail, for example, in the publications below: U.S. Pat. Nos. 4,050,938, 4,239,843, 4,241,154, 4,242,429, 4,241,155, 4,242,430, 4,273,854, 4,246,329, 4,271,253, 4,242,431, 4,248,949, 4,245,195, 4,268,605, 4,246,330, 4,269,926, 4,245,018, 4,301,223, 4,343,886, 4,346,165, 4,590,153; JP-A 81/167 138, 81/168 652, 82/30 834, 82/161 744; EP-A 137 271, 161 577, 185 506; DE-A 2 853 865.

The photographic layers may also contain hydroquinone compounds. These act as light stabilizers for the colour couplers and for the colour images and as scavengers of oxidized developer in the intermediate layers. They are used in particular in the magenta layer. Hydroquinone compounds of this type and combinations thereof with other additives are described in greater detail, for example, in the publications below: U.S. Pat. Nos. 2,360,290, 2,336,327, 2,403,721, 2,418,613, 2,675,314, 2,701,197, 2,710,801, 2,732,300, 2,728,659, 2,735,765, 2,704,713, 2,937,086, 2,816,028, 3,582,333, 3,637,393, 3,700,453, 3,960,570, 3,935,016, 3,930,866, 4,065,435, 3,982,944, 4,232,114, 4,121,939, 4,175,968, 4,179,293, 3,591,381, 3,573,052, 4,279,990, 4,429,031, 4,346,165, 4,360,589, 4,346,167, 4,385,111, 4,416,978, 4,430,425, 4,277,558, 4,489,155, 4,504,572, 4,559,297, FR-A 885 982; GB-A 891 158, 1 156 167, 1 363 921, 2 022 274, 2 066 975, 2 071 348, 2 081 463, 2 117 526, 2 156 091; DE-A 2 408 168, 2 726 283, 2 639 930, 2 901 520, 3 308 766, 3 320 483, 3 323 699; DD-A 216 476,214 468, 214 469, EP-A 84 290, 110 214, 115 305, 124 915, 124 877, 144 288, 147 747, 178 165, 161 577; JP-A 75/33 733, 75/21 249, 77/128 130, 77/146 234, 79/70 036, 79/133 131, 81/83 742, 81/87 040, 81/109 345, 83/134 628, 82/22 237, 82/112 749, 83/17 431, 83/21 249, 84/75 249, 84/149 348, 84/182 785, 84/180 557, 84/189 342, 84/228 249, 84/101 650, 79/24 019, 79/25 823, 86/48 856, 86/48 857, 86/27 539, 86/6652, 86/72 040, 87/11 455, 87/62 157, and in Research Disclosure 79/17 901, 79/17 905, 79/18 813, 83/22 827 and 84/24 014.

The photographic layers may also contain further derivatives of hydroquinone ethers. These compounds act as light stabilizers and are particularly suitable for stabilising magenta dyes. Such compounds and combinations thereof with other additives are described in greater detail, for example, in the publications below:

U.S. Pat. No. 3,285,937, 3,432,300, 3,519,429, 3,476,772, 3,591,381, 3,573,052, 3,574,627, 3,573,050, 3,698,909, 3,764,337, 3,930,866, 4,113,488, 4,015,990, 4,113,495, 4,120,723, 4,155,765, 4,159,910, 4,178,184, 4,138,259, 4,174,220, 4,148,656, 4,207,111, 4,254,216, 4,134,011, 4,273,864, 4,264,720, 4,279,990, 4,332,886, 4,436,165, 4,360,589, 4,416,978, 4,385,111, 4,459,015, 4,559,297, 4,631,252, 4,616,082; GB-A 1 347 556, 1 366 441, 1 547 392, 1 557 237, 2 135 788; DE-A 3 214 567, 4 008 785, 4 012 305; DD-214 469, EP-A 161 577, 167 762, 164 130, 176 845; JP-A 76/123 642, 77/35 633, 77/147 433, 78/126, 78/10 430, 78/53 321, 79/24 019, 79/25 823, 79/48 537, 79/44 521, 79/56 833, 79/70 036, 79/70 830, 79/73 032, 79/95 233, 79/145 530, 80/21 004, 80/50 244, 80/52 057, 80/70 840, 80/139 383, 81/30 125, 81/151 936, 82/34 552, 82/68 833, 82/204 306, 82/204 037, 83/134 634, 83/207 039, 84/60 434, 84/101 650, 84/87 450, 84/149 348, 84/182 785, 86/72 040, 87/11 455, 87/62 157, 87/63 149, 86/2151, 86/6652, 86/48 855, 89/309 058 and in Research Disclosure 78/17 05 1.

Preferred co-stabilizers conform to the following formulae P, SA, SB, HQ, RE, KA and KB.

Compounds of formula P

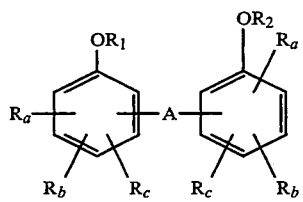

where
$R_1$ and $R_2$, independently of one another, are hydrogen, acyl or alkyl;
$R_a$, $R_b$ and $R_c$, independently of one another, are H, alkyl, cycloalkyl, aryl, halogen, alkoxy, aroxy, acyloxy, alkylthio, arylthio, acyl, sulphonyl, sulphamoyl, acylamino, sulphonylamino or nitro;
A is a bond, $S=[O]_m$, alkylene or $NR_d$;
$R_d$ is alkyl or acyl; and
m is 0, 1 or 2.

Examples of compounds of formula P:

P1
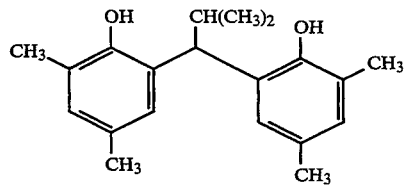

P2
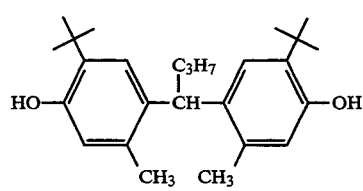

P3
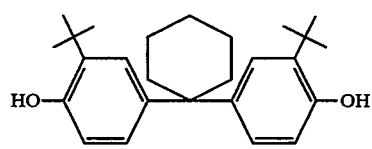

-continued

P4
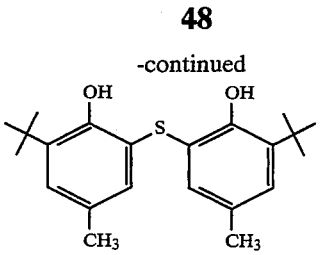

P5
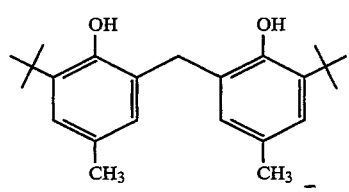

P6
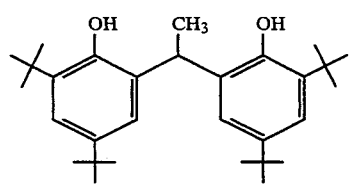

P7
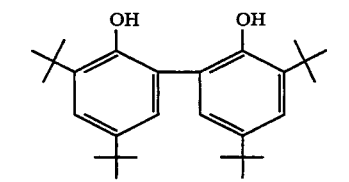

P8
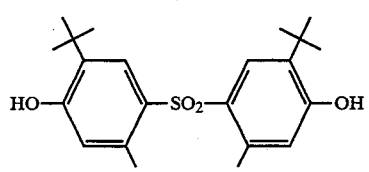

P9
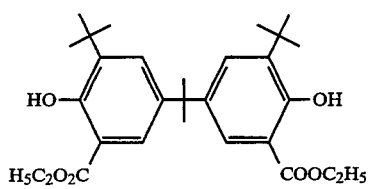

P10
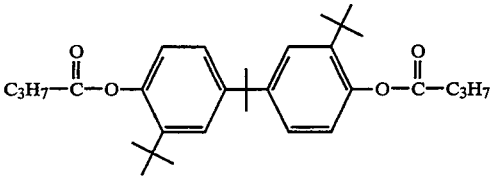

P11
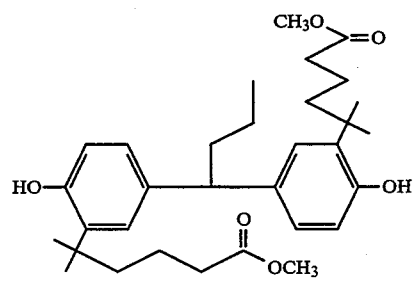

-continued
P12 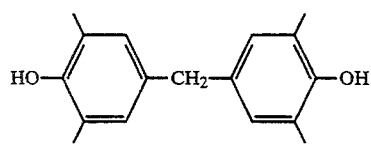
P13 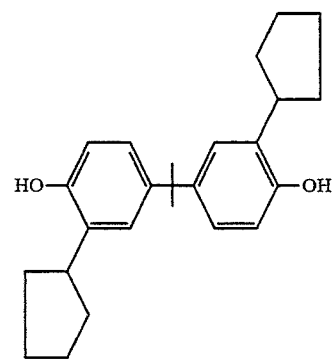
P14 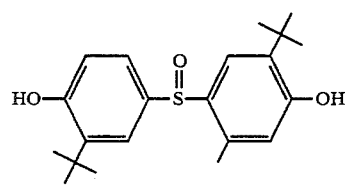
P15 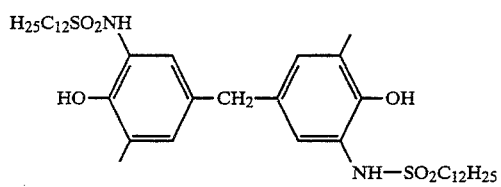
P16 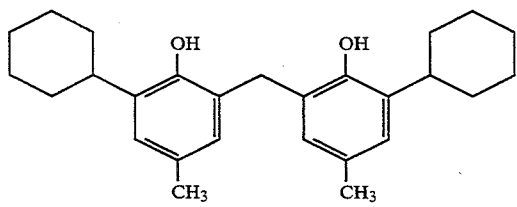
P17 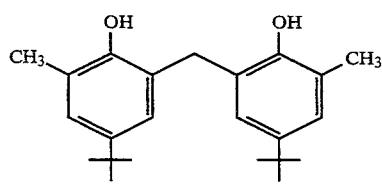
-continued
P18 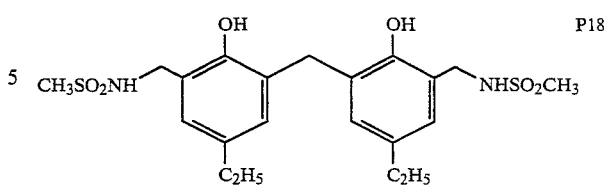
P19 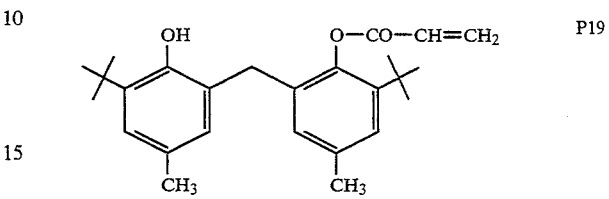
P20 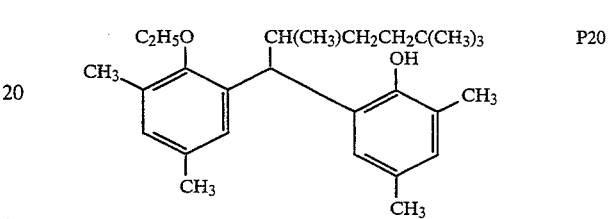
P21 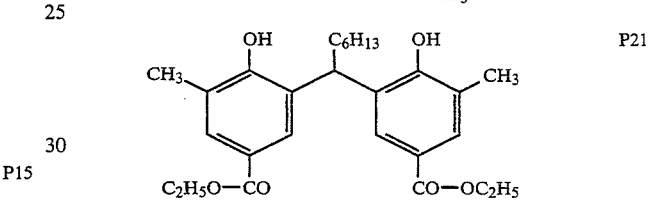
Compounds of formula SA
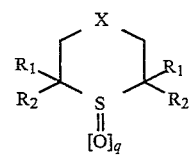
where
- $R_1$ is hydrogen;
- $R_2$ is phenyl or
- $R_1$ and $R_2$ are methyl;
- q is 0, 1 or 2; and
- X is a divalent radical, which completes the ring in formula SA to give a tetrahydrothiopyrane.
Examples of compounds of formula SA (see also U.S. Pat. No. 4,993,271):
SA1 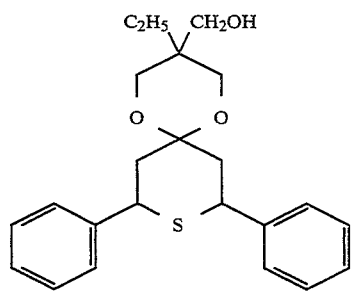

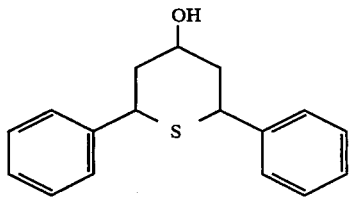
SA2

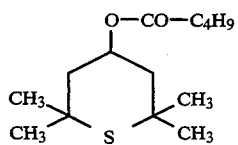
SA3

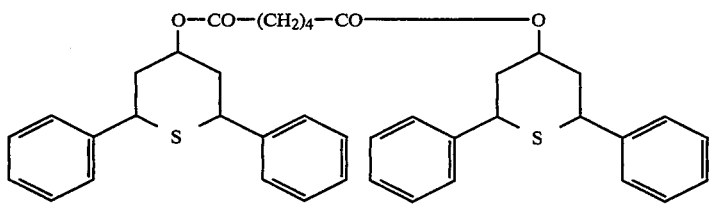
SA4

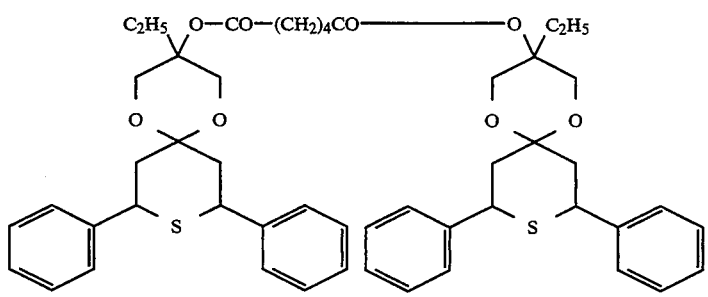
SA5

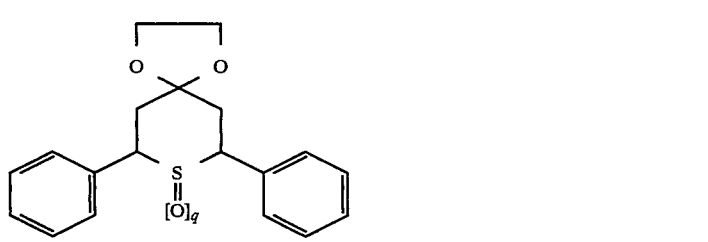
SA6

Compounds of formula SB
$R_3$—S—$(C_pH_{2p})$—Z—$R_4$
where
$R_3$ is alkyl, aryl or a group $(C_pH_{2p})$—Z—$R_4$;
p is 1–12;
Z is —CO—O— or —O—CO—;
$R_4$ is a mono-, di-, tri- or tetra-valent group.
Examples of compounds of the formula SB $C_{12}H_{25}$—S—$CH_2CH_2CO$—O—$C_4H_9$  SB1

$S(CH_2CH_2CO$—$OC_4H_9)_2$  SB2

SB3

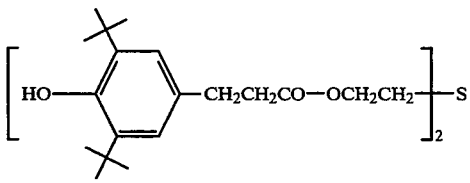

$[C_{12}H_{25}SCH_2CH_2CO$—O—$CH_2]_4\!\!-\!\!C$  SB4

Compounds of the formula HQ

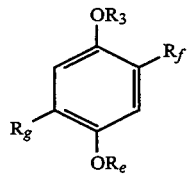

where
$R_e$ and $R_d$, independently of one another, are alkyl or cycloalkyl; and
$R_f$ and $R_g$, independently of one another, are as $R_a$, $R_b$ and $R_c$.
Examples of compound of the formula HQ HQ1 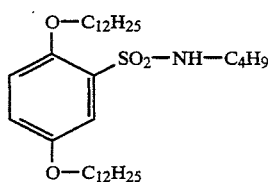

HQ2 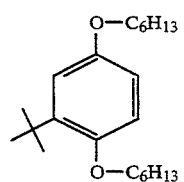

HQ3 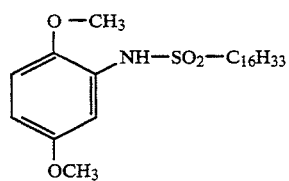

HQ4 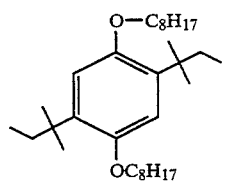

HQ5 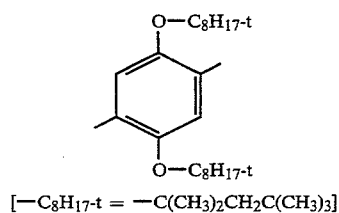

[—C₈H₁₇-t = —C(CH₃)₂CH₂C(CH₃)₃]

HQ6 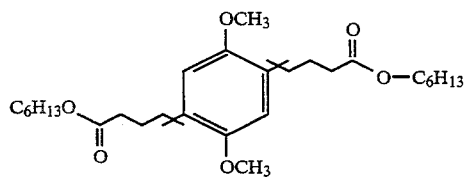

HQ7 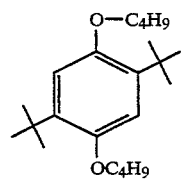

HQ8 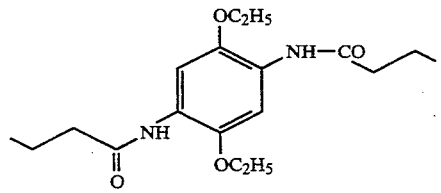

Compounds of the formula RE

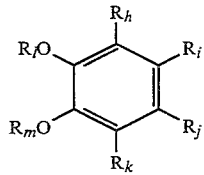

where

R$_l$ and R$_m$, independently of one another, are H, acyl or alkyl; or R$_l$ and R$_m$ are bound together to a P—O-aryl radical; and R$_h$, R$_i$, R$_j$ and R$_k$, independently of one another, are as R$_a$, R$_b$ and R$_e$, provided that at least one of the radicals R$_i$ or R$_j$ is not alkyl.

Examples of compounds of the formula RE

RE1 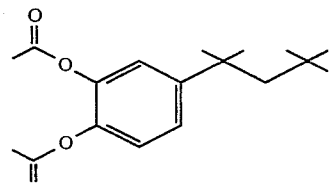

RE2 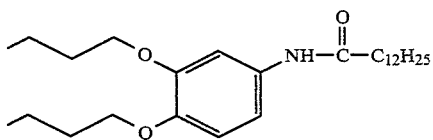

RE3 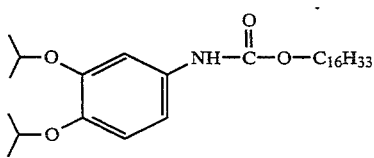

RE4 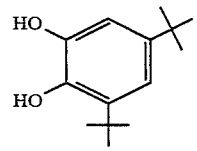

RE5 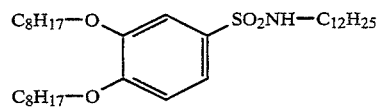

RE6 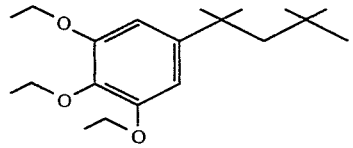

RE7 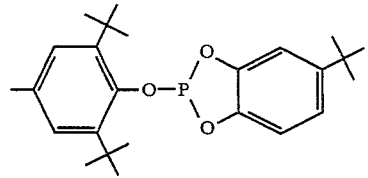

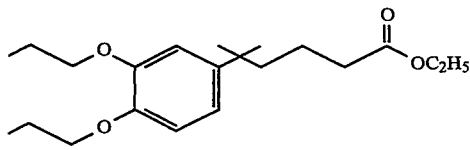

Compounds of formula KA

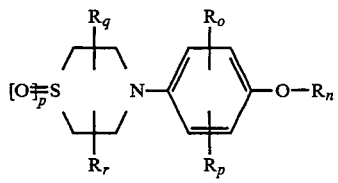

where
 $R_n$ is alkyl, cycloalkyl or aryl;
 p is 0, 1 or 2; and
 $R_o$, $R_p$, $R_q$ and $R_r$, independently of one another, are as $R_a$, $R_b$ and $R_c$.
Examples of compounds of the formula KA KA1
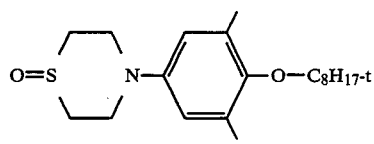

KA2
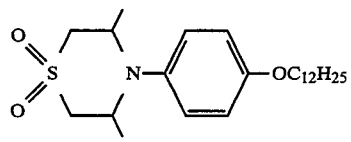

KA3
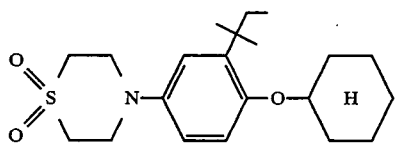

KA4
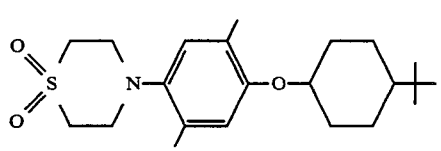

KA5
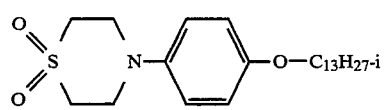

KA6
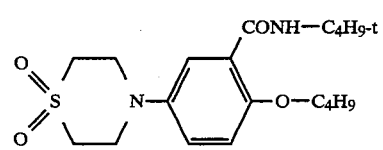

KA7
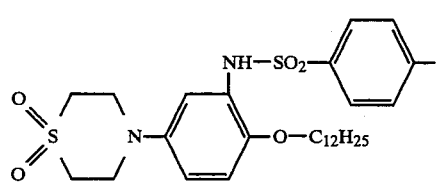

Compounds of formula KB

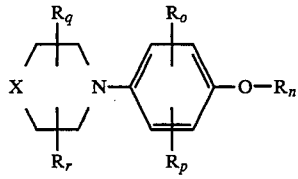

where,
 X is a bond, $$-\underset{R_s}{\underset{|}{CH}}-, \quad -O-, \quad -\overset{O}{\underset{\|}{C}}- \quad \text{or} \quad -\underset{}{\overset{R_t}{\underset{|}{N}}};$$

$R_t$ is alkyl, aryl, acyl or sulphonyl; and
$R_s$ is as $R_a$, $R_b$ and $R_c$.
Examples of compounds of the formula KB KB1
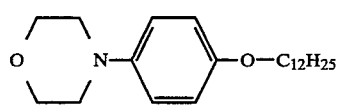

KB2
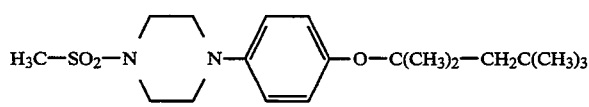

KB3
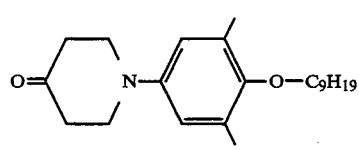

KB4

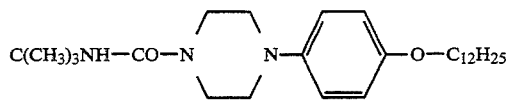
KB5

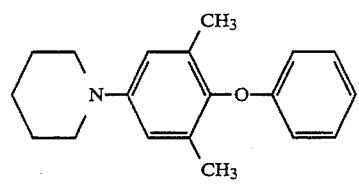
KB6

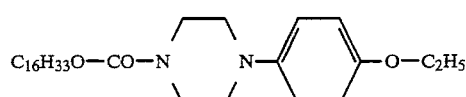
KB7

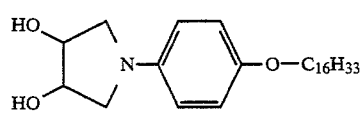
KB8

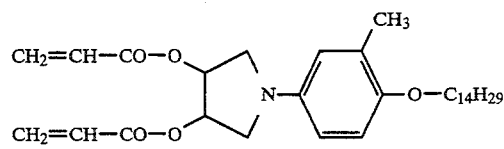
KB9

Silver-halide emulsions which can be used are conventional silver-chloride, silver-bromide or silver-iodide emulsions or mixtures thereof, such as silver-chlorobromide and silver-chloroiodide emulsions, in which the silver halides may have any known crystal form. The use of silver-chloride emulsions is particularly important in the material according to the invention. The preparation of such emulsions and the sensitization thereof are described in RESEARCH DISCLOSURE, November 1989, No. 307 105. This publication furthermore mentions a number of binders for said emulsions which can also be used in the materials according to the invention. The same applies to the bases mentioned in the publication.

The silver-halide emulsion which can be used for carrying out this invention can be sensitized for all desired wavelengths with the aid of sensitization pigments. For this purpose, it is possible to use cyanine pigments, merocyanine pigments, holopolar pigments, hemicyanine pigments, styryl pigments or hemioxanol pigments.

The photographic layers may furthermore contain conventional plasticizers, such as glycerol. The emulsions may also be cured by means of curing agents which are customary for gelatin. Finally, the emulsions may also contain customary coating auxiliaries.

The present invention thus furthermore relates to colour-photographic recording materials according to claim 1, which contain further organic stabilizers, UV absorbers, optical brighteners, light stabilizers, colour cast inhibitors and/or plasticizers.

The present invention also relates to compounds of the formula

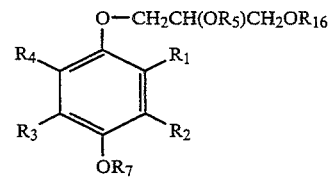
(Ia)

in which
$R_1$ and $R_3$, independently of one another, are hydrogen, $C_1-C_{12}$alkyl, $C_5-C_7$cycloalkyl, which is unsubstituted or substituted by one or two $C_1-C_4$alkyl groups, phenyl-$C_1-C_4$alkyl, phenyl, $C_1-C_4$alkoxy or a group of the formula V

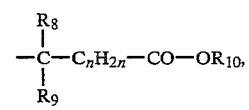
V in which $R_8$ and $R_9$, independently of one another, are $C_1-C_8$alkyl,
n is 1–10, and
$R_{10}$ is hydrogen, $C_1-C_{24}$alkyl, which is unsubstituted or interrupted by one or more O atoms and is unsubstituted or substituted by one —OH, or is $C_2-C_{18}$alkenyl, $C_5-C_{12}$cycloalkyl, which is unsubstituted or substituted by 1 to 3 $C_1-C_4$alkyl, or is phenyl, which is unsubstituted or substituted by one or two $C_1-C_4$alkyl, or is phenyl-$C_1-C_4$alkyl or furfuryl;

$R_2$ and $R_4$, independently of one another, are hydrogen or $C_1$–$C_4$alkyl;

$R_5$ is hydrogen, —CO—$R_{11}$, —CO—O$R_{12}$ or —Si($R_{13}$)($R_{14}$)($R_{15}$), in which $R_{11}$ is $C_1$–$C_{18}$alkyl or phenyl, $R_{12}$ is $C_1$–$C_4$alkyl, and $R_{13}$, $R_{14}$ and $R_{15}$, independently of one another, are $C_1$–$C_6$alkyl or phenyl; $R_7$ is hydrogen, $C_1$–$C_{12}$alkyl, which is uninterrupted or interrupted by one or more —O—, —S— or —SO$_2$—, or is $C_5$–$C_{12}$cycloalkyl, which is unsubstituted or substituted by 1 to 3 $C_1$–$C_4$alkyl, or is phenyl-$C_1$–$C_4$alkyl, a group of the formula VI

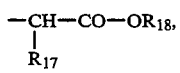

or a group of the formula VIIa

in which $R_5$ and $R_{16}$ are as defined for formula (Ia), $R_{17}$ is hydrogen or $C_1$–$C_{18}$alkyl, and $R_{18}$ is $C_1$–$C_{12}$alkyl, which is unsubstituted or interrupted by one or more O atoms, or is $C_2$–$C_{18}$alkenyl, benzyl or phenyl, which is unsubstituted or substituted by 1–3

$C_1$–$C_4$alkyl; and the radicals $R_{16}$, independently of one another, are hydrogen, $C_1$–$C_{18}$alkyl, $C_2$–$C_{18}$alkenyl, phenyl-$C_1$–$C_4$alkyl, $C_3$–$C_{24}$alkyl or $C_2$–$C_{14}$hydroxyalkyl, each of which is interrupted by one or more O atoms, or are phenyl, tolyl, $C_5$–$C_6$cycloalkyl, which is unsubstituted or substituted by 1 to 3 $C_1$–$C_8$alkyl, or —CO—$R_{11}$, in which $R_{11}$ is $C_1$–$C_{18}$alkyl or phenyl.

Preferred compounds are those of the formula

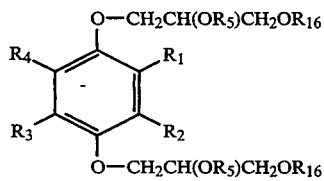

in which $R_1$ and $R_3$, independently of one another, are hydrogen, $C_1$–$C_{12}$alkyl, $C_5$–$C_6$cycloalkyl, which is unsubstituted or substituted by one or two $C_1$–$C_4$alkyl groups, phenyl-$C_1$–$C_4$alkyl, phenyl, $C_1$–$C_8$alkoxy or a group of the formula V

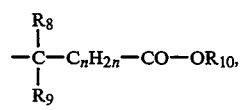

in which $R_8$ and $R_9$, independently of one another, are $C_1$–$C_8$alkyl;

n is 1–10, and $R_{10}$ is hydrogen, $C_1$–$C_{24}$alkyl, which is unsubstituted or interrupted by one or more O atoms and unsubstituted or substituted by one —OH, or is $C_2$–$C_{18}$alkenyl, $C_5$–$C_{12}$cycloalkyl, which is unsubstituted or substituted by 1 to 3 $C_1$–$C_4$alkyl, or is phenyl, which is unsubstituted or substituted by one or two $C_1$–$C_4$alkyl, or is phenyl-$C_1$–$C_4$alkyl or furfuryl;

$R_2$ and $R_4$, independently of one another, are hydrogen or $C_1$–$C_{12}$alkyl;

$R_5$ is hydrogen, —CO—$R_{11}$, —CO—O$R_{12}$ or —Si($R_{13}$)($R_{14}$)($R_{15}$), in which $R_{11}$ is $C_1$–$C_{12}$alkyl, $R_{12}$ is $C_1$–$C_4$alkyl, and $R_{13}$, $R_{14}$ and $R_{15}$, independently of one another, are $C_1$–$C_6$alkyl or phenyl; and the radicals $R_{16}$, independently of one another, are $C_1$–$C_{18}$alkyl, $C_2$–$C_{10}$alkenyl, benzyl, $C_3$–$C_{18}$alkyl which is interrupted by one or more O atoms, cyclohexyl or —CO—$R_{11}$, in which $R_{11}$ is $C_1$–$C_{12}$alkyl.

Particular preference is given to compounds of the formula

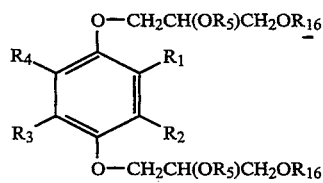

in which $R_1$ and $R_3$, independently of one another, are hydrogen, $C_1$–$C_{12}$alkyl, $C_5$–$C_6$cycloalkyl, which is unsubstituted or substituted by one or two $C_1$–$C_4$alkyl groups, phenyl-$C_1$–$C_4$alkyl, phenyl, $C_1$–$C_8$alkoxy or a group of the formula V

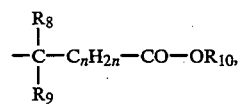

in which $R_8$ and $R_9$, independently of one another, are $C_1$–$C_8$alkyl;

n is 1–10, and $R_{10}$ is hydrogen, $C_1$–$C_{24}$alkyl, which is unsubstituted or interrupted by one or more O atoms and is unsubstituted or substituted by one —OH, or is $C_2$–$C_{18}$alkenyl, $C_5$–$C_{12}$cycloalkyl, which is unsubstituted or substituted by 1 to 3 $C_1$–$C_4$alkyl, or is phenyl, which is unsubstituted or substituted by one or two $C_1$–$C_4$alkyl, or is phenyl-$C_1$–$C_4$alkyl or furfuryl;

$R_2$ and $R_4$, independently of one another, are hydrogen or $C_1$–$C_{12}$alkyl;

$R_5$ is hydrogen, —CO—$R_{11}$, —CO—O$R_{12}$ or —Si($R_{13}$)($R_{14}$)($R_{15}$), in which $R_{11}$ is $C_1$–$C_4$alkyl, $R_{12}$ is $C_1$–$C_4$alkyl, and $R_{13}$, $R_{14}$ and $R_{15}$, independently of one another, are $C_1$–$C_6$alkyl or phenyl; and the radicals $R_{16}$, independently of one another, are $C_1$–$C_{18}$alkyl, allyl, benzyl, $C_3$–$C_{12}$alkyl which is interrupted by one or more O atoms, cyclohexyl or —CO—$R_{11}$, in which $R_{11}$ is $C_1$–$C_4$alkyl.

Very particularly preference is given to compounds of the formula

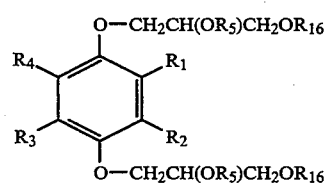

in which $R_1$, $R_3$ and $R_4$, independently of one another, are hydrogen or $C_1$-$C_8$alkyl;

$R_2$ is hydrogen;

$R_5$ is hydrogen or —CO—CH$_3$; and the radicals $R_{16}$, independently of one another, are $C_1$-$C_{12}$alkyl, allyl or $C_3$-$C_7$alkyl which is interrupted by 1–3 O atoms.

The present invention furthermore relates to compounds of the formulae III

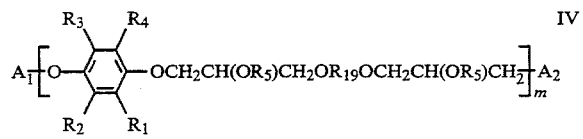

III and IV

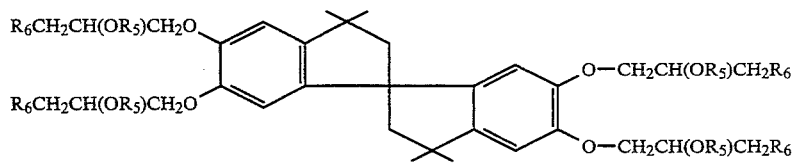

IV in which
$R_1$, $R_2$, $R_3$, $R_4$, $R_5$, $R_6$, $R_{19}$, $A_1$, $A_2$ and m are as defined in claim 1.

Further preferred compounds are those mentioned in the description of the photographic material.

The compounds according to the invention can be prepared by methods known per se, for example by reacting a compound of one of the formulae

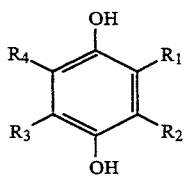

I°

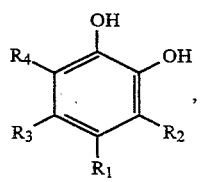

II° with a glycidyl ether of the formula

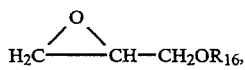

in which the radicals $R_1$, $R_2$, $R_3$, $R_4$ and $R_{16}$ are as defined in claim 1.

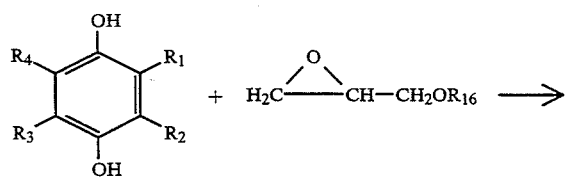

-continued

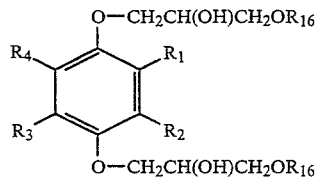

Compounds according to the invention in which $R_5$ is not hydrogen can be prepared by further reacting with an acylating agent or silylating agent, for example

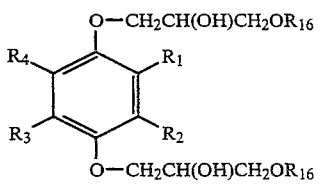

+ Cl—COCH$_3$ 

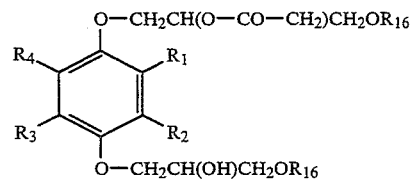

The polymeric compounds of the formula (IV) can be prepared by reacting a compound of the formula (I°) with a bisglycidyl ether of the formula

The examples below illustrate the invention in greater detail.

EXAMPLE 1

Preparation of 1,4-di(3'-butoxy-2'-hydroxypropoxy)-2,5-dimethylbenzene 20 g of 2,5-dimethylhydroquinone, 42.2 g of butyl glycidyl ether and 5.3 g of ethyltriphenylphosphonium bromide are stirred for 15 hours in 80 ml of boiling xylene. The mixture is then allowed to cool to room temperature, the organic phase is washed with water and dried, and the solvent is evaporated. The crude product is chromatographed on silica gel, giving 27.5 g of 1,4-di(3'-butoxy-2'-hydroxypropoxy)-2,5-dimethylbenzene as a yellowish oil (m.p. <30° C.).

Elemental analysis: $C_{22}H_{38}O_6$ Calculated: C 66.30; H 9.61% Found: C 66.00; H 9.70 %

EXAMPLE 2

If Example 1 is repeated, but with the 2,5-dimethylhydroquinone replaced by the corresponding amount of 2,5-di-tert-butylhydroquinone, 28.7 g of 1,4-di(3'- butoxy-2'-hydroxypropoxy)-2,5-di-tert-butylbenzene are obtained as a white solid (m.p. 59° C.)

Elemental analysis: $C_{28}H_{50}O_6$ Calculated: C 69.67; H 10.44 % Found: C 69.31; H 10.41%

EXAMPLES 1a and 2a

A procedure analagous to Examples 1 and 2 gives the compounds 1–48 mentioned above, which have a melting point of <20° C., with the exception of Compounds 1 (59°–60° C.), 2 (76° C.), 12 (40°–41° C.), 13 (58°–60°), 26 (131° C.), 30 (116°–123° C.) and 37 (31°–32° C.).

EXAMPLE 3

A polyethylene-coated support material is coated with a gelatin layer containing silver bromide, magenta coupler (M-6) and a stabilizer.

The gelatin layer contains the following components (per $m^2$ of support material):

TABLE 1

| Component | Ag Br layer |
|---|---|
| Gelatin | 5.15 g |
| Curing agent | 300 mg |
| Wetting agent | 85 mg |
| Silver bromide | 260 mg |
| Magenta coupler | 325 mg |
| Tricresyl phosphate | 162 mg |
| Stabilizer | 114 mg |

The curing agent used is 2,4-dichloro-6-hydroxytriazine, and the wetting agent used is the sodium salt of diisobutylnapthalenesulfonic acid.

A step wedge having a density difference of 0.15 logE per step is exposed onto each of the resultant samples, which are subsequently processed in accordance with the manufacturer's instructions by the Kodak EP2 process for colour negative papers.

After exposure and processing, the remission density in green for the magenta step is measured at a density between 0.9 and 1.1 of the wedge. The wedge is then exposed behind a UV absorber filter in an Atlas exposure unit with 15 $kJ/cm^2$, and the remission density is re-measured. The drop in magenta dye density ($-\Delta D$) is shown in Table 2 in %.

TABLE 2

| Sample No. | Stabilizer | $-\Delta D$ |
|---|---|---|
| 1 | none | 87 |
| 2 | 3 | 53 |
| 3 | 14 | 54 |

EXAMPLE 4

The procedure is as in Example 3, but the Kodak RA4 process is used. The drop in magenta dye density ($-\Delta D$) is shown in Table 3 in %.

TABLE 3

| Sample No. | Stabilizer | $-\Delta D$ |
|---|---|---|
| 4 | none | 81 |
| 5 | 14 | 44 |

It can be seen from Examples 3 and 4 that the novel compounds are good light stabilizers.

EXAMPLE 5

The procedure is as in Example 3, but the stabilizer is used as an oil. The amounts of oil are shown in Table 4. A second step wedge is measured in blue in order to determine the yellowing. The wedge is then stored for 28 days in a conditioning cabinet at 75° C. and 60 % relative humidity, the remission density (in blue) is re-measured, and the increase in yellow dye density ($-\Delta D_B$) is calculated.

The drop in magenta dye density ($-\Delta D$) in % and the yellowing ($-\Delta D_B$) are shown in Table 4. The drop in dye density ($-\Delta D$) is also shown for a magenta dye density of 2 in Table 4.

TABLE 4

| Sample No | Oil | Amount (mg/$m^2$) | $-\Delta D$ (%) D = 1 | $-\Delta D$ (%) D = 2 | $-\Delta D_B$ |
|---|---|---|---|---|---|
| 6 | Tricresyl phosphate | 276 | 84 | 81 | 0.12 |
| 7 | Tricresyl phosphate | 325 | 82 | 78 | 0.11 |
| 8 | Tricresyl phosphate | 440 | 79 | 71 | 0.11 |
| 9 | 14 | 276 | 60 | 57 | 0.11 |
| 10 | 14 | 325 | 45 | 33 | 0.12 |
| 11 | 14 | 440 | 40 | 22 | 0.12 |

It can be seen that the drops in dye density for D=1 and D=2 are much lower than for the conventional oil tricresyl phosphate. Climatic yellowing of the stabilizer (oil) of the invention is, within the limit of experimental accuracy, the same as that for the conventional oil (tricresyl phosphate).

EXAMPLE 6

The procedure is as in Example 5, but 306 mg of the magenta coupler (M-5) are used. The Atlas yellowing is also measured; to this end, the remission density in blue is measured in order to determine the yellowing. The wedge is then exposed in an Atlas exposure unit with 30 $kJ/cm^2$, the remission density (in blue) is re-measured, and the increase in yellow dye density ($-\Delta D_B$) is calculated. The drop in magenta dye density ($-\Delta D$) after 30 $kJ/cm^2$ exposure and the yellowing ($-\Delta D_B$) are shown in Table 5.

TABLE 5

| Sample No. | Oil | Amount (mg/$m^2$) | $-\Delta D$ | $-\Delta D_B$ |
|---|---|---|---|---|
| 12 | Tricresyl phosphate | 612 | 42 | 0.02 |
| 13 | 14 | 612 | 8 | 0.00 |
| 14 | 14 | 918 | 7 | 0.00 |

It can be seen that, here too, the novel compounds are very highly suitable as a photographic oil having light stabilization properties for magenta couplers/dyes.

EXAMPLE 7

The procedure is as in Example 3, but the novel compounds are used as oils (325 mg/$m^2$) for further light stabilizers. The further light stabilizer used conforms to the formula:

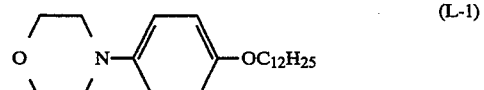

(L-1)

and is employed in an amount of 114 mg/$m^2$. The drop in magenta dye density ($-\Delta D$) and the climatic yellowing ($-\Delta D_B$) are shown in Table 6.

TABLE 6

| Sample No. | Oil | Stabilizer | $-\Delta D$ | $-\Delta D_B$ |
|---|---|---|---|---|
| 15 | Tricresyl phosphate | — | 82 | 0.11 |

TABLE 6-continued

| Sample No. | Oil | Stabilizer | −ΔD | −ΔD_B |
|---|---|---|---|---|
| 16 | Tricresyl phosphate | L-1 | 50 | 0.19 |
| 17 | 14 | — | 45 | 0.12 |
| 18 | 14 | L-1 | 38 | 0.18 |

It can be seen that the novel compounds not only act as light stabilizers, but are also suitable as coupler solvents (oils).

EXAMPLE 8

The procedure is as in Example 3, but the Kodak RA4 process is used, magenta coupler M-11 (204 mg) is used, the stabilizer is employed in an amount of 102 mg, and a 30 kJ/cm2 exposure is carried out. The drop in magenta dye density is shown in Table 7 in %.

TABLE 7

| Sample No. | Stabilizer | −ΔD (%) |
|---|---|---|
| 19 | none | 91 |
| 20 | 16 | 56 |
| 21 | 32/k | 59 |

EXAMPLE 9

The procedure is as in Example 8, but the stabilizer is used as an oil (408 mg,/m²), and no tricresyl phosphate is employed in samples 23–25. The drop in magenta dye density is shown in Table 8 in %.

TABLE 8

| Sample No. | Oil | −ΔD (%) |
|---|---|---|
| 22 | Tricresyl phosphate | 92 |
| 23 | 16 | 36 |
| 24 | 14 | 34 |
| 25 | 32/j | 34 |

EXAMPLE 10

The procedure is as in Example 9, but the amount of oil is 204 mg/m², and no tricresyl phosphate is employed in samples 27 and 28. The drop in magenta dye density is shown in Table 9 in %.

TABLE 9

| Sample No. | Oil | −ΔD (%) |
|---|---|---|
| 26 | Tricresyl phosphate | 91 |
| 27 | 14 | 40 |
| 28 | 32/c | 32 |

EXAMPLE 11

The procedure is as in Example 10, but the novel compounds are used as an oil (204 mg/m²) for further stabilizers. The further stabilizers used conform to the formulae

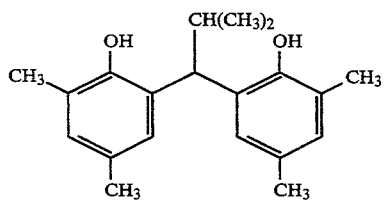

P 1

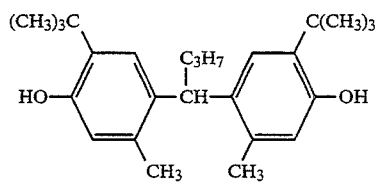

P 2

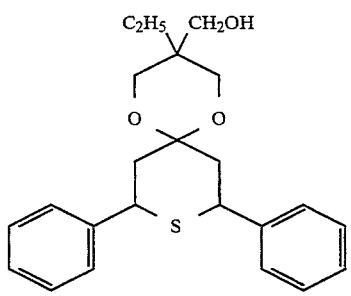

SA 1 and are employed in an amount of 102 mg/m², and no tricresyl phosphate is employed in samples 33–39. The drop in magenta dye density is shown in Table 10 in %.

TABLE 10

| Sample No. | Oil | Stabilizer | −ΔD (%) |
|---|---|---|---|
| 29 | Tricresyl phosphate | — | 91 |
| 30 | Tricresyl phosphate | P 1 | 55 |
| 31 | Tricresyl phosphate | P 2 | 70 |
| 32 | Tricresyl phosphate | SA 1 | 88 |
| 33 | 14 | — | 40 |
| 34 | 14 | P 1 | 24 |
| 35 | 14 | P 2 | 30 |
| 36 | 14 | SA 1 | 28 |
| 37 | 32/c | — | 32 |
| 38 | 32/c | P 1 | 22 |
| 39 | 32/c | SA 1 | 23 |

What is claimed is:

1. A colour-photographic recording material which contains a magenta coupler and, as stabilizer, at least one compound of the formula

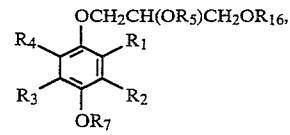

I

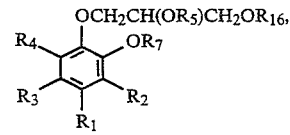

II

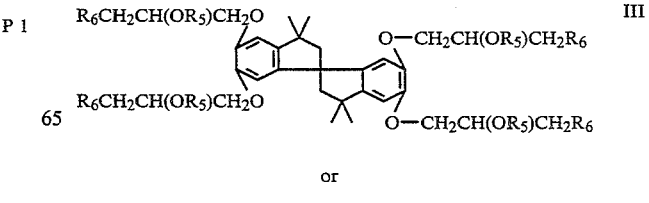

III or

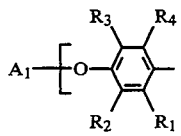

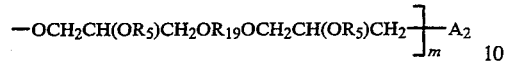

where
R₁ and R₃, independently of one another, are hydrogen, $C_1$-$C_{12}$alkyl, $C_5$-$C_7$cycloalkyl, which is unsubstituted or substituted by one or two $C_1$-$C_4$alkyl groups, phenyl-$C_1$-$C_4$alkyl, phenyl, $C_1$-$C_4$alkoxy or a group of the formula V

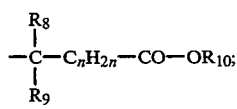

in which R₈ and R₉, independently of one another, are $C_1$-$C_8$alkyl,
n is 1–10, and
R₁₀ is hydrogen, $C_1$-$C_{24}$alkyl, which is unsubstituted or interrupted by one or more O atoms and is unsubstituted or substituted by one —OH group, or is $C_2$-$C_{18}$alkenyl, $C_5$-$C_{12}$cycloalkyl, which is unsubstituted or substituted by 1 to 3 $C_1$-$C_4$alkyl, or is phenyl, which is unsubstituted or substituted by one or two $C_1$-$C_4$alkyl, or is phenyl-$C_1$-$C_4$alkyl or furfuryl;
R₂ and R₄, independently of one another, are hydrogen or $C_1$-$C_{12}$alkyl;
R₅ is hydrogen, —CO—R₁₁, —CO—OR₁₂ or —Si(R₁₃)(R₁₄)(R₁₅), in which R₁₁ is $C_1$-$C_{18}$alkyl, $C_2$-$C_{18}$alkenyl or phenyl, R₁₂ is $C_1$-$C_4$alkyl and R₁₃, R₁₄ and R₁₅, independently of one another, are $C_1$-$C_6$alkyl or phenyl; the radicals R₆, independently of one another, are —OR₁₆ or $C_1$-$C_{15}$alkyl, in which R₁₆ is hydrogen, $C_1$-$C_{18}$alkyl, $C_2$-$C_{18}$alkenyl, phenyl-$C_1$-$C_4$alkyl, $C_3$-$C_{24}$alkyl or $C_2$-$C_{14}$hydroxyalkyl, each of which is interrupted by one or more O atoms, or is phenyl, which is unsubstituted or substituted by $C_1$-$C_4$alkyl, $C_1$-$C_4$alkoxy or halogen, tolyl, $C_5$-$C_6$cycloalkyl, which is unsubstituted or substituted by 1 to 3 $C_1$-$C_8$alkyl, or is —CO—R₁₁, in which R₁₁ is $C_1$-$C_{18}$alkyl, $C_2$-$C_{18}$alkenyl or phenyl;
R₇ is a group of the formula VI

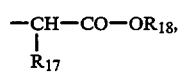

or a group of the formula VII

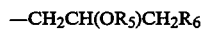

in which R₅ and R₆ are as defined for formula I,
R₁₇ is hydrogen or $C_1$-$C_{18}$alkyl, and
R₁₈ is $C_1$-$C_{12}$alkyl, which is unsubstituted or interrupted by one or more O atoms, or is $C_2$-$C_{18}$alkenyl, benzyl or phenyl, which is unsubstituted or substituted by 1–3 $C_1$-$C_4$alkyl;

R₁₉ is $C_2$-$C_{10}$alkylene, phenylene or a -phenylene-R₂₀-phenylene- group, in which R₂₀ is —O—, —S—, —SO₂—, —CH₂— or —C(CH₃)₂—;
m is 1–100;
A₁ is hydrogen, —CH₂CH(OR₅)CH₂OR₁₉OCH(OR₅)CH₂OR₅ or

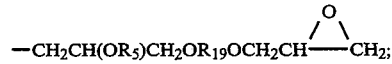

and
A₂ is —OH or

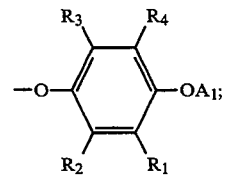

or R₃ and R₇ in the formula I, together with the atoms to which they are bonded, form a $C_5$-$C_6$ ring, which is unsubstituted or substituted by 1 to 3 $C_1$-$C_8$alkyl.

2. A colour-photographic recording material according to claim 1, which contains, as stabilizer, at least one compound of the formula

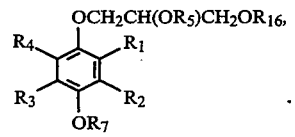

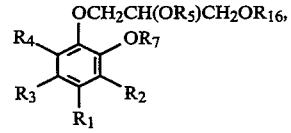

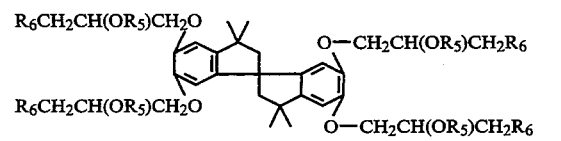

or

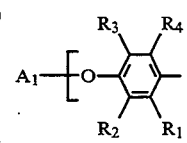

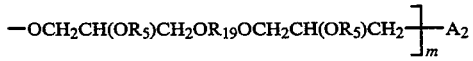

in which R₁ and R₃, independently of one another, are hydrogen, $C_1$-$C_8$alkyl, cyclohexyl, —C(CH₃)₂C₆H₅, $C_1$-$C_4$alkoxy or a group of the formula V

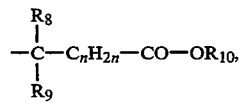

in which $R_5$ and $R_9$ are methyl;

n is 3, and $R_{10}$ is hydrogen, $C_1$-$C_{12}$alkyl, which is unsubstituted or interrupted by one or more O atoms and is unsubstituted or substituted by one —OH, or is $C_2$-$C_{18}$alkenyl or benzyl;

$R_2$ is hydrogen;

$R_4$ is hydrogen or $C_1$-$C_8$alkyl;

$R_5$ is hydrogen, —CO—$R_{11}$, —CO—$OR_{12}$ or —Si($R_{13}$)($R_{14}$)($R_{15}$), in which $R_{11}$ is $C_1$-$C_{18}$alkyl, $C_2$-$C_{18}$alkenyl or phenyl, $R_{12}$ is $C_1$-$C_4$alkyl, and $R_{13}$, $R_{14}$ and $R_{15}$, independently of one another, are $C_1$-$C_6$alkyl or phenyl; the radicals $R_6$ independently of one another, are —$OR_{16}$, in which $R_{16}$ is and $A_2$ is —OH or

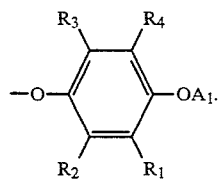

3. A colour-photographic recording material according to claim 1, which contains, as stabilizer, at least one compound of the formula

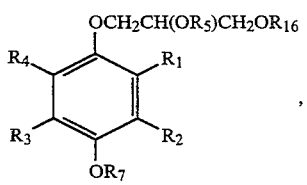

I

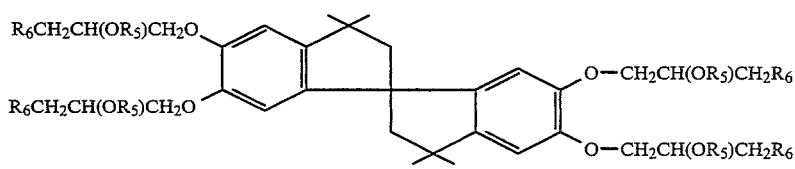

III

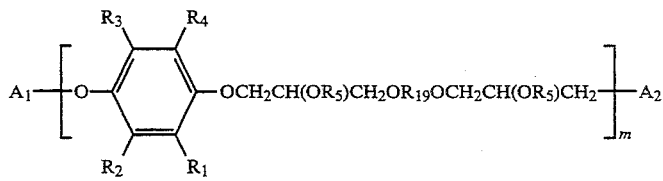

IV hydrogen, $C_1$-$C_{18}$alkyl, $C_2$-$C_{18}$alkenyl, phenyl-$C_1$-$C_4$alkyl, $C_3$-$C_{24}$alkyl or $C_2$-$C_{14}$hydroxyalkyl, each of which is interrupted by one or more O atoms, or is phenyl, tolyl, $C_5$-$C_6$cycloalkyl, which is unsubstituted or substituted by 1 to 3 $C_1$-$C_8$alkyl, or is —CO—$R_{11}$, in which $R_{11}$ is $C_1$-$C_{18}$alkyl, $C_2$-$C_{18}$alkenyl or phenyl;

$R_7$ is a group of the formula VI

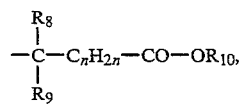

VI or a group of the formula VII

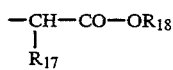

VII, in which $R_5$ and $R_6$ are as defined for formula I, $R_{17}$ is hydrogen or $C_1$-$C_{12}$alkyl, and $R_{18}$ is $C_1$-$C_8$alkyl;

$R_{19}$ is $C_2$-$C_8$alkylene, phenylene or a -phenylene-$R_{20}$-phenylene- group, in which $R_{20}$ is —$SO_2$—, —$CH_2$— or —$C(CH_3)_2$—;

m is 1–50;

$A_1$ is hydrogen, —$CH_2CH(OR_5)CH_2OR_{19}OCH(OR_5)CH_2OR_5$ or

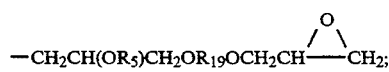

in which $R_1$ and $R_3$, independently of one another, are hydrogen, $C_1$-$C_8$alkyl, $C_1$-$C_4$alkoxy or a group of the formula V

V in which $R_8$ and $R_9$ are methyl, n is 3, and $R_{10}$ is $C_1$-$C_4$alkyl;

$R_2$ is hydrogen;

$R_4$ is hydrogen or $C_1$-$C_8$alkyl;

$R_5$ is hydrogen, CO—$R_{11}$, —$COOR_{12}$ or —Si($R_{13}$)($R_{14}$)($R_{15}$), in which $R_{11}$ is $C_1$-$C_4$alkyl or $C_2$-$C_3$alkenyl, $R_{12}$ is $C_1$-$C_4$alkyl, and $R_{13}$, $R_{14}$ and $R_{15}$, independently of one another, are $C_1$-$C_6$alkyl; the radicals $R_6$, independently of one another, are —$OR_{16}$, in which $R_{16}$ is $C_1$-$C_{18}$alkyl, allyl, benzyl, phenyl, $C_3$-$C_{12}$alkyl which is interrupted by one or more O atoms, or is cyclohexyl or —CO—$R_{11}$, in which $R_{11}$ is $C_1$-$C_4$alkyl or $C_2$-$C_3$alkenyl;

$R_7$ is a group of the formula VII

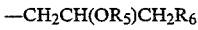

VII, in which $R_5$ and $R_6$ are as defined for formula I;

$R_{19}$ is $C_2$-$C_8$alkylene or a phenylene-$R_{20}$-phenylene-group, in which $R_{20}$ is —$C(CH_3)_2$—;

m is 1-25;

$A_1$ is hydrogen, $-CH_2CH(OR_5)CH_2OR_{19}OCH(OR_5)CH_2OR_5$ or

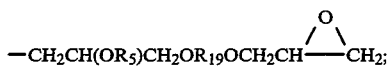

and $A_2$ is —OH or

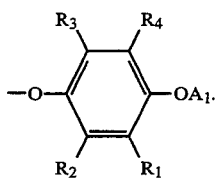

4. A colour-photographic recording material according to claim 1, which contains, as stabilizer, at least one compound of the formula

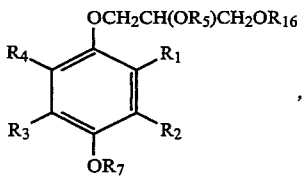    I in which $R_1$, $R_3$ and $R_4$, independently of one another, are hydrogen or $C_1$-$C_8$alkyl;

$R_2$ is hydrogen;

$R_5$ is hydrogen or —CO—$CH_3$;

$R_{16}$ is $C_1$-$C_{12}$alkyl, allyl or $C_3$-$C_7$alkyl which is interrupted by 1-3 O atoms; and $R_7$ is a group of the formula VII

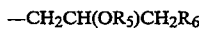    VII, in which $R_5$ is as defined for formula I and $R_6$ is —$OR_{16}$.

5. A colour-photographic recording material according to claim 1, which contains, as stabilizer, at least one compound of the formula

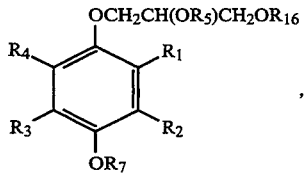    I in which $R_1$, $R_3$ and $R_4$, independently of one another, are hydrogen or $C_1$-$C_8$alkyl;

$R_2$ is hydrogen;

$R_5$ is hydrogen;

$R_{16}$ is $C_1$-$C_{12}$alkyl, and $R_7$ is a group of the formula VII

    VII, in which $R_5$ is as defined for formula I and $R_6$ is —$OR_{16}$.

6. A colour-photographic recording material according to claim 1, which contains further organic stabilizers, UV absorbers, optical brighteners, light stabilizers, colour cast inhibitors and/or plasticizers.

7. A colour-photographic recording material according to claim 1, which contains at least one further organic stabilizer of one of the following formulae P, SA, SB, HQ, RE, KA or KB formula P

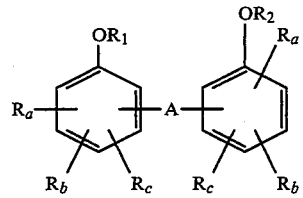

where $R_1$ and $R_2$, independently of one another, are hydrogen, acyl or alkyl;

$R_a$, $R_b$ and $R_c$, independently of one another, are H, alkyl, cycloalkyl, aryl, halogen, alkoxy, aroxy, acyloxy, alkylthio, arylthio, acyl, sulphonyl, sulphamoyl, acylamino, sulphonylamino or nitro;

A is a bond, $S=O_m$, alkylene or $NR_d$;

$R_d$ is alkyl or acyl; and m is 0, 1 or 2;

formula SA

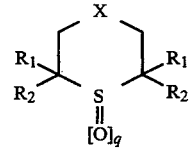

where $R_1$ is hydrogen;

$R_2$ is phenyl or $R_1$ and $R_2$ are methyl;

q is 0, 1 or 2; and

X is a divalent radical, which completes the ring in formula SA to give a tetrahydrothiopyrane;

formula SB $R_3-S-(C_pH_{2p})-Z-R_4$ where $R_3$ is alkyl, aryl or a group $(C_pH_{2p})-Z-R_4$;

p is 1-12;

Z is —CO—O— or —O—CO—;

$R_4$ is a mono-, di-, tri- or tetra-valent group;

formula HQ

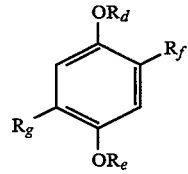

where $R_e$ and $R_d$, independently of one another, are alkyl or cycloalkyl; and $R_f$ and $R_g$, independently of one another, are as $R_a$, $R_b$ and $R_c$;

formula RE

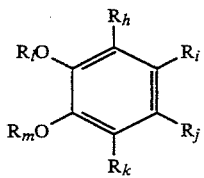

where
 $R_l$ and $R_m$, independently of one another, are H, acyl or alkyl; or $R_l$ and $R_m$ are bound together to a P—O-aryl radical; and
 $R_h$, $R_i$, $R_j$ and $R_k$, independently of one another, are as $R_a$, $R_b$ and $R_c$, provided that at least one of the radicals $R_i$ or $R_j$ is not alkyl;
formula KA

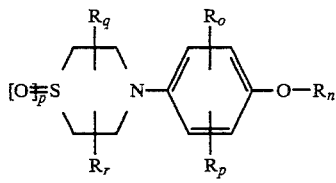

where
 $R_n$ is alkyl, cycloalkyl or aryl;

p is 0, 1 or 2; and
 $R_o$, $R_p$, $R_q$ and $R_r$, independently of one another, are as $R_a$, $R_b$ and $R_c$;
formula KB

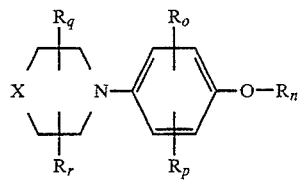

where,
 X is a bond,

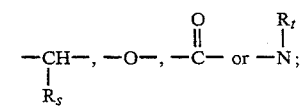

$R_t$ is alkyl, aryl, acyl or sulphonyl; and
 $R_s$ is as $R_a$, $R_b$ and $R_c$.

8. A process for stabilizing magenta couplers and/or magenta dyes in colour-photographic materials, in which a stabilizer according to claim 1 is incorporated into the material.

* * * * *